(12) United States Patent
Bergnes et al.

(10) Patent No.: US 7,161,002 B2
(45) Date of Patent: Jan. 9, 2007

(54) SYNTHESES OF QUINAZOLINONES

(75) Inventors: Gustave Bergnes, Pacifica, CA (US);
Edward Ha, San Francisco, CA (US);
George Yiannikourous, Florence, SC (US); Panos Kalaritis, Florence, SC (US); Brandon E. Yonce, Florence, SC (US); Kurt Alan Welday, Jr., Hartsville, SC (US)

(73) Assignees: Cytokinetics, Inc., South San Francisco, CA (US); SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 11/254,211

(22) Filed: Oct. 20, 2005

(65) Prior Publication Data
US 2006/0041130 A1 Feb. 23, 2006

Related U.S. Application Data

(62) Division of application No. 10/366,828, filed on Feb. 14, 2003, now Pat. No. 7,009,049.

(60) Provisional application No. 60/380,746, filed on May 14, 2002, provisional application No. 60/357,244, filed on Feb. 15, 2002.

(51) Int. Cl.
*C07D 239/00* (2006.01)
*C07D 239/70* (2006.01)

(52) U.S. Cl. ...................................... 544/253; 544/286
(58) Field of Classification Search ............... 544/253, 544/286
See application file for complete search history.

(56) References Cited

U.S. PATENT DOCUMENTS

| | | | |
|---|---|---|---|
| 3,320,124 A | 5/1967 | Waletzky et al. |
| 3,322,756 A | 5/1967 | Ruschig et al. |
| 3,723,432 A | 3/1973 | Ott et al. |
| 3,740,442 A | 6/1973 | Ott et al. |
| 3,925,548 A | 12/1975 | Oh |
| 3,962,244 A | 6/1976 | Weyer et al. |
| 4,011,324 A | 3/1977 | Althuis |
| 4,281,127 A | 7/1981 | LaMahieu et al. |
| 4,729,996 A | 3/1988 | Wright et al. |
| 4,734,419 A | 3/1988 | Hashimoto et al. |
| 4,808,590 A | 2/1989 | Higa et al. |
| 4,857,530 A | 8/1989 | Berman et al. |
| 4,859,670 A | 8/1989 | Kampe et al. |
| 4,866,084 A | 9/1989 | Gunasekera et al. |
| 4,970,226 A | 11/1990 | Sun et al. |
| 4,981,856 A | 1/1991 | Hughes |
| 4,992,550 A | 2/1991 | Hughes |
| 5,037,829 A | 8/1991 | Freyne et al. |
| 5,081,124 A | 1/1992 | Hughes |
| 5,147,875 A | 9/1992 | Coates |
| 5,158,959 A | 10/1992 | Geiger et al. |
| 5,187,167 A | 2/1993 | Hughes |
| 5,204,354 A | 4/1993 | Chakravarty et al. |
| 5,264,439 A | 11/1993 | Greenlee et al. |
| 5,280,027 A | 1/1994 | Andrew et al. |
| 5,316,906 A | 5/1994 | Haughland et al. |
| 5,330,987 A | 7/1994 | Allen et al. |
| 5,342,944 A | 8/1994 | Mohan et al. |
| 5,401,766 A | 3/1995 | Geiger et al. |
| 5,430,148 A | 7/1995 | Webber et al. |
| 5,444,061 A | 8/1995 | Bisset et al. |
| 5,449,678 A | 9/1995 | Pines et al. |
| 5,470,878 A | 11/1995 | Michnick et al. |
| 5,492,915 A | 2/1996 | Dereu et al. |
| 5,561,133 A | 10/1996 | Bisset et al. |
| 5,574,057 A | 11/1996 | Ireland et al. |
| 5,707,992 A | 1/1998 | Webber et al. |
| 5,714,493 A | 2/1998 | Myers et al. |
| 5,747,498 A | 5/1998 | Schnur et al. |
| 5,753,664 A | 5/1998 | Aono et al. |
| 5,756,450 A | 5/1998 | Hahn et al. |
| 5,756,502 A | 5/1998 | Padia |
| 5,756,510 A | 5/1998 | Griffin et al. |
| 5,770,595 A | 6/1998 | Klein et al. |

(Continued)

FOREIGN PATENT DOCUMENTS

AU  B-12617/88  9/1988

(Continued)

OTHER PUBLICATIONS

Chemcats Copyright 2000 ACS, 1998:596123 CHEMCATS, Maybridge, Apr. 3, 2000, DP 01489, "N2-(3-pyridylmethyl)-4-oxo-3,4-dihydroquinazoline-2-carboxamide," 190437-46-8, Chemical Library.

(Continued)

*Primary Examiner*—Thurman K. Page
*Assistant Examiner*—Chukwuma Nwaonicha
(74) *Attorney, Agent, or Firm*—Finnegan, Henderson, Farabow, Garrett & Dunner, LLP

(57) ABSTRACT

The present invention provides novel quinazolinone compositions of matter comprising enantiomerically pure compound represented by Formula I:

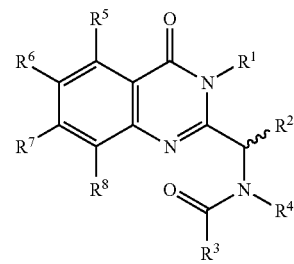

or a pharmaceutically acceptable salt thereof, having a detectable amount of one or more starting material and/or reagent used in the synthesis thereof.

12 Claims, No Drawings

U.S. PATENT DOCUMENTS

| | | | |
|---|---|---|---|
| 5,773,476 A | 6/1998 | Chen et al. |
| 5,777,115 A | 7/1998 | Leigh et al. |
| 5,780,476 A | 7/1998 | Underiner |
| 5,783,577 A | 7/1998 | Houghten et al. |
| 5,789,427 A | 8/1998 | Chen et al. |
| 5,795,898 A | 8/1998 | Brown et al. |
| 5,801,181 A | 9/1998 | Michnick et al. |
| 5,801,182 A | 9/1998 | Klein et al. |
| 5,804,584 A | 9/1998 | Underiner |
| 5,807,861 A | 9/1998 | Klein et al. |
| 5,807,862 A | 9/1998 | Klein et al. |
| 5,811,429 A | 9/1998 | Connell et al. |
| 5,817,662 A | 10/1998 | Klein et al. |
| 5,837,703 A | 11/1998 | Kumar et al. |
| 5,852,024 A | 12/1998 | Pines et al. |
| 5,859,018 A | 1/1999 | Brown et al. |
| 5,869,665 A | 2/1999 | Padia |
| 5,885,996 A | 3/1999 | Webber et al. |
| 5,891,879 A | 4/1999 | Nagler et al. |
| 5,892,114 A | 4/1999 | Goldmann et al. |
| 5,922,866 A | 7/1999 | Miyata et al. |
| 5,929,081 A | 7/1999 | Brown et al. |
| 5,939,421 A | 8/1999 | Palanki et al. |
| 5,948,775 A | 9/1999 | Koko et al. |
| 5,948,784 A | 9/1999 | Fujiwara et al. |
| 6,008,010 A | 12/1999 | Greenberger et al. |
| 6,136,812 A | 10/2000 | Chenard et al. |
| 6,156,758 A | 12/2000 | Kung et al. |
| 6,207,403 B1 | 3/2001 | Goldstein et al. |
| 6,245,768 B1 | 6/2001 | He et al. |
| 6,545,004 B1 | 4/2003 | Finer et al. |
| 6,545,005 B1 | 4/2003 | Baxter et al. |
| 6,559,160 B1 | 5/2003 | Schall et al. |
| 6,562,831 B1 | 5/2003 | Finer et al. |
| 6,613,798 B1 | 9/2003 | Porter et al. |
| 6,627,755 B1 | 9/2003 | Chenard et al. |
| 6,630,479 B1 | 10/2003 | Finer et al. |
| 6,753,428 B1 | 6/2004 | Bergnes et al. |
| 6,794,379 B1 | 9/2004 | Medina et al. |
| 6,831,085 B1 | 12/2004 | Bergnes et al. |
| 7,009,049 B1 | 3/2006 | Bergnes et al. |
| 2001/0046997 A1 | 11/2001 | Abraham et al. |
| 2002/0032207 A1 | 3/2002 | Thompson et al. |
| 2002/0055519 A1 | 5/2002 | Thompson et al. |
| 2002/0165221 A1 | 11/2002 | Baxter et al. |
| 2002/0169159 A1 | 11/2002 | Medina et al. |
| 2002/0198326 A1 | 12/2002 | Aoyama et al. |
| 2003/0018038 A1 | 1/2003 | Thompson et al. |
| 2003/0055054 A1 | 3/2003 | Medina et al. |
| 2003/0091946 A1 | 5/2003 | Uchira et al. |
| 2003/0119834 A1 | 6/2003 | Bamdad |
| 2003/0119854 A1 | 6/2003 | Schall et al. |
| 2003/0130293 A1 | 7/2003 | Bamdad |
| 2003/0139398 A1 | 7/2003 | Hoekstra et al. |
| 2003/0139457 A1 | 7/2003 | Baxter et al. |
| 2003/0144350 A1 | 7/2003 | Stevenson et al. |
| 2003/0158188 A1 | 8/2003 | Lee et al. |
| 2003/0158198 A1 | 8/2003 | Lee et al. |
| 2003/0166933 A1 | 9/2003 | Bergnes et al. |
| 2003/0171387 A1 | 9/2003 | Sun et al. |
| 2003/0195211 A1 | 10/2003 | Sadhu et al. |
| 2003/0220338 A1 | 11/2003 | Watkins et al. |
| 2003/0220356 A1 | 11/2003 | Ibrahim et al. |
| 2004/0023996 A1 | 2/2004 | Finer et al. |
| 2004/0048853 A1 | 3/2004 | Bergnes |
| 2004/0067969 A1 | 4/2004 | Bergnes et al. |
| 2004/0077662 A1 | 4/2004 | Zhou et al. |
| 2004/0077667 A1 | 4/2004 | Matsuoka et al. |
| 2004/0077668 A1 | 4/2004 | Feng et al. |
| 2004/0082567 A1 | 4/2004 | McDonald et al. |
| 2004/0092561 A1 | 5/2004 | Ruckie et al. |
| 2004/0116438 A1 | 6/2004 | Lu et al. |
| 2004/0142949 A1 | 7/2004 | Bergnes et al. |
| 2004/0192913 A1 | 9/2004 | Bergnes et al. |
| 2004/0198724 A1 | 10/2004 | NcNaughton-Smith et al. |
| 2004/0242596 A1 | 12/2004 | Kim et al. |
| 2004/0259826 A1 | 12/2004 | Fraley et al. |
| 2005/0059823 A1 | 3/2005 | McNaughton-Smith et al. |
| 2005/0152940 A1 | 7/2005 | Hezi-Yamit et al. |
| 2005/0209254 A1 | 9/2005 | Wang et al. |
| 2006/0041130 A1 | 2/2006 | Bergnes et al. |

FOREIGN PATENT DOCUMENTS

| | | |
|---|---|---|
| EP | 0 056 637 A1 | 7/1982 |
| EP | 0 286 813 A2 | 2/1988 |
| EP | 0 341 990 A3 | 11/1989 |
| EP | 0 341 990 B1 | 11/1989 |
| EP | 0 360 417 A2 | 3/1990 |
| EP | 0 360 417 A3 | 3/1990 |
| EP | 0 373 891 A2 | 6/1990 |
| EP | 0 431 945 A2 | 6/1991 |
| EP | 0 481 614 A1 | 4/1992 |
| EP | 0 512 676 A1 | 11/1992 |
| EP | 0 534 706 A1 | 3/1993 |
| EP | 0 537 937 A2 | 4/1993 |
| EP | 0 884 310 A1 | 12/1998 |
| EP | 0 884 316 A1 | 12/1998 |
| EP | 0 884 319 A2 | 12/1998 |
| EP | 0 884 319 A3 | 12/1998 |
| EP | 0 900 568 A2 | 3/1999 |
| EP | 0 903 344 A1 | 3/1999 |
| EP | 1 072 952 A1 | 1/2000 |
| EP | 1 174 430 A1 | 1/2002 |
| GB | 2271111 A | 4/1994 |
| HU | 184797 | 10/1984 |
| JP | 62-135473 | 6/1987 |
| JP | 06049070 A2 | 2/1994 |
| JP | 06-148835 | 5/1994 |
| WO | WO 91/12001 A1 | 8/1991 |
| WO | WO 93/11115 A2 | 6/1993 |
| WO | WO 93/23404 A1 | 11/1993 |
| WO | WO 94/21259 A1 | 9/1994 |
| WO | WO 95/16682 A1 | 6/1995 |
| WO | WO 95/24379 A1 | 9/1995 |
| WO | WO 96/06616 A1 | 3/1996 |
| WO | WO 96/19224 A1 | 6/1996 |
| WO | WO 96/28444 A1 | 9/1996 |
| WO | WO 96/39403 A1 | 12/1996 |
| WO | WO 97/10221 A1 | 3/1997 |
| WO | WO 97/43276 A1 | 11/1997 |
| WO | WO 98/26664 A1 | 6/1998 |
| WO | WO 98/29410 A1 | 7/1998 |
| WO | WO 98/34613 A1 | 8/1998 |
| WO | WO 98/58947 A1 | 12/1998 |
| WO | WO 99/08501 A2 | 2/1999 |
| WO | WO 00/00491 A1 | 1/2000 |
| WO | WO 00/07017 A2 | 2/2000 |
| WO | WO 01/74344 A2 | 10/2000 |
| WO | WO 00/69827 A1 | 11/2000 |
| WO | WO 01/16114 A2 | 3/2001 |
| WO | WO 01/19800 A2 | 3/2001 |
| WO | WO 01/23364 A1 | 4/2001 |
| WO | WO 01/23365 A1 | 4/2001 |
| WO | WO 01/25235 A1 | 4/2001 |
| WO | WO 01/30768 A1 | 5/2001 |
| WO | WO 01/32171 A1 | 5/2001 |
| WO | WO 01/32634 A1 | 5/2001 |
| WO | WO 01/42216 A2 | 6/2001 |
| WO | WO 01/66519 A2 | 9/2001 |
| WO | WO 01/70737 A2 | 9/2001 |
| WO | WO 01/74344 A2 | 10/2001 |
| WO | WO 01/81346 * | 11/2001 |
| WO | WO 01/81346 A2 | 11/2001 |

| | | |
|---|---|---|
| WO | WO 01/95884 A2 | 12/2001 |
| WO | WO 01/98278 * | 12/2001 |
| WO | WO 01/98278 A1 | 12/2001 |
| WO | WO 02/04444 A2 | 1/2002 |
| WO | WO 02/08224 A1 | 1/2002 |
| WO | WO 02/09713 A2 | 2/2002 |
| WO | WO 02/09713 A3 | 2/2002 |
| WO | WO 02/14319 A2 | 2/2002 |
| WO | WO 02/083143 A1 | 10/2002 |
| WO | WO 02/094790 A1 | 11/2002 |
| WO | WO 03/027234 A2 | 4/2003 |
| WO | WO 03/035076 A1 | 5/2003 |
| WO | WO 03/035077 A1 | 5/2003 |
| WO | WO 03/039460 A2 | 5/2003 |
| WO | WO 03/043995 A1 | 5/2003 |
| WO | WO 03/049527 A2 | 6/2003 |
| WO | WO 03/049678 A2 | 6/2003 |
| WO | WO 03/049679 A2 | 6/2003 |
| WO | WO 03/050064 A2 | 6/2003 |
| WO | WO 03/050122 A2 | 6/2003 |
| WO | WO 03/063800 A2 | 8/2003 |
| WO | WO 03/070701 A2 | 8/2003 |
| WO | WO 03/070701 A3 | 8/2003 |
| WO | WO 03/076418 A1 | 9/2003 |
| WO | WO 03/079973 A2 | 10/2003 |
| WO | WO 03/094839 A2 | 11/2003 |
| WO | WO 03/097053 A1 | 11/2003 |
| WO | WO 03/099211 A2 | 12/2003 |
| WO | WO 03/103575 A2 | 12/2003 |
| WO | WO 03/105855 A1 | 12/2003 |
| WO | WO 03/106417 A1 | 12/2003 |
| WO | WO 03/106426 A1 | 12/2003 |
| WO | WO 03/106435 A1 | 12/2003 |
| WO | WO 2004/004652 A2 | 1/2004 |
| WO | WO 2004/006916 A1 | 1/2004 |
| WO | WO 2004/009036 A2 | 1/2004 |
| WO | WO 2004/018058 A2 | 3/2004 |
| WO | WO 2004/020599 A2 | 3/2004 |
| WO | WO 2004/022554 A1 | 3/2004 |
| WO | WO 2004/034972 A2 | 4/2004 |
| WO | WO 2004/039774 A2 | 5/2004 |
| WO | WO 2004/064741 A2 | 8/2004 |
| WO | WO 2004/078758 | 9/2004 |

OTHER PUBLICATIONS

Q. Kozhevnikov et al. 4-Quinazolinones. II. 2-(Aminomethyl)-3-acyl-4-quinazolinones. (Russian) Tr Perm Sel-Khoz Inst. 79: 66-72 (1971). Chem Abstracts 78: 390 (1973).
Gupta, C.M. et al. "Drugs acting on the central nervous system. Synthesis of substituted quinazolones and quinazolones and triazepino- and triazocinoquinazolones," *J. Med. Chem.* 11: 392-395 (1968).
Saari, W.S. et al. "Synthesis and evaluation of 2-pyridinone derivatives as HIV-1-specific reverse transcriptase inhibitors. 2. Analogues of 3-aminopyridin-2(1H)-one," *J. Med. Chem.* 35: 3792-3802 (1992).
Farghaly, A.M. et al. "Non-steroidal anti-inflammatory agents. III: Synthesis of pyrazole derivatives of 4(3H)-quinazolinones," *Alexandria J. Pharm. Sci.* 4(1): 52-56 (1990).
Dymek, W. et al. "2-Chloromethyl-6-methylquinazolone-4 and its transformations," *Diss. Pharm. Et Pharmacol.* 20(1): 29-34 (1968).
Pattanaik, J.M. et al. "Synthesis and fungicidal activity of 3-aryl-2-(4'-aryl thiazol-2'-ylaminomethyl) quinazol-4(3H)-ones," *Indian J. Chem.* 37B: 1304-1306 (1998).
Gupta, D.P.,e t al. "Thiazolidinones, azetidinones and formazans of quinazolinones," *Indian J. Chem.* 26B: 1197-1199 (1987).
Parasharya, P.M. et al. "4 (3H)-Quinazolones. Part I: 2-Alkyl/arylaminomethyl-3-p-hydroxy/methoxyphenyl-4(3H)-quinazolones," *J. Inst. Chemists (India)* 64: 184-185 (1992).
Parasharya, P.M. et al. "4-(3H)-Quinazolones: 2-N-aryl/alkyl-amino-methyl/ethyl-3-p-hydroxyphenyl/p-anisyl/p-arylaminoacyloxyphenyl/p-N-arylcarbamoylmethoxyphenyl-4-(3H)-quinazolones," *J. Inst. Chemists (India)* 64: 238-241 (1992).
Matthews, N. et al. "Structure-activity relationships of phenothiazines in inhibiting lymphocyte motility as determined by a novel flow cytometric assay," *Biochem. Pharmcol.* 50(7): 1053-1061 (1995).
Debnath, A.K. "Structure-Based Identification of Small Molecule Antiviral Compounds Targeted to the gp41 Core Structure of the Human Immunodeficiency Virus Type 1," *J. Med. Chem.* 42 (17): 3203-3209 (1999).
Bocskei, Z. et al.. "Two Antithrombotic Quinazolone Derivatives." *Acta Crystallogr., Sect. C: Cryst. Struct. Commun.* C51(4): 723-726 (1995).
Szabó, M. et al. "Synthesis of Potential CCK Antagonist Quinazolone Derivatives," Chemical Abstracts, vol. 124, No. 13, Abstract No. 176002v (1996).
Ager et al. "Synthesis and Central Nervous System Activity of Quinozolones Related to 2-Methyl-3-(*o-tolyl*)-4(3H) quinazolone (Methaqualone)," *J. Med. Chem.* 20(3): 379-386 (1977).
Tlwari et al. "Synthesis and CNS Activity of 2-Aryl-3(3'-, 4'-Dihydroxyphenylethyl) 6-8-substituted-4 (3H)Quinazolinones," *Indian J. Pharm. Sci.* pp. 40-43 (1978).
Rao et al. "Synthesis and Biological Activities of Certain Derivatives of 3-Aryl-4(3H)-quinazolinones, Part-II," *J. Indian Chem. Soc.* LXII: 234-237 (1985).
Registry file compounds from unspecified chemical libraries. Commercially available from ComGenex, Sep. 16, 1999.
Registry File Compounds from Published References, Maybridge Catalog, Apr. 3, 2000.
Singh et al. Chemical Abstracts, vol. 92, Abstracts No. 58712 (1980).
Spirkova et al., Chemical Abstracts, vol. 132, Abstract No. 35672 (1999).
Pandey et al. Chemical Abstracts, vol. 124, Abstract No. 331723 (1996).
Parasharya et al. Chemical Abstracts, vol. 121, Abstract No. 108675 (1994).
Saari et al. Chemical Abstracts, vol. 117, Abstract No. 191731 (1992).
Farghaly et al. Chemical Abstracts, vol. 114, Abstract No. 122242 (1991).
El-Nasser Ossman et al. Chemical Abstracts, vol. 106, Abstract No. 207516 (1987).
Rao et al. Chemical Abstracts, vol. 105, Abstract No. 97416 (1986).
Gupta et al. Chemical Abstracts, vol. 69, Abstract No. 42637 (1968).
Kumar et al. Chemical Abstracts, vol. 102, Abstract No. 142800 (1985).
Chaurasia et al. Chemical Abstracts, vol. 96, Abstract No. 6681 (1982).
Tani et al. Chemical Abstracs, vol. 93, Abstract No. 26374 (1980).
Ager et al. Chemical Abstracts, vol. 86, Abstract No. 83505 (1977).
Kozhevnikov et al. Chemical Abstracts, vol. 78, Abstract No. 16128U (1971).
Bergman et al. "Synthesis of Chrysogine, a Metabolite of *Penicilium chrysogenum* and some related 2-substituted 4-(3H)-Quinazolinones," *Tetrahedron* 46: 1295-1310 (1990).
Hart et al. "Synthesis of (–)-Alantrypinone," *Tet. Lett.* 40: 5429-5432 (1999).
Hart et al. "Synthesis of *ent*-Alantrypinone" *J. Am. Chem. Soc.* 123: 5892-5899 (2001).
Mayer et al. "Solid phrase synthesis of quinazolinones" *Tet. Lett.* 38(49):8445-8448 (1997).
Prashad et al. "Reaction of benzoyleneurea and isatoic anhydride with the Vilsmeier reagent" *Tel. Lett.* 38(8):1313-1316 (1997).
Villalgordo et al. "Solid-phase synthesis of 3H-quinazolin-4-ones based on an aza Wittig-mediated annulation strategy" *Synlett* 1405-1407 (1998).
Wuckelt et al. "Efficient synthesis of quinazolin-4-ones and axially chiral 2,2'-bis-quinazolin-4-ones by reaction of anthranilic acid derived nucleophiles with oxalic acid-bis(imidoyl)chlorides." *Synlett* 7:1100-1102 (1999).

Wang et al. "Total synthesis of the quinazolinone alkaloids (−)-Fumiquinazoline G and (−)-Fiscalin B" *J. Org. Chem.* 63:2432-2433 (1998).

Padia et al. "Novel nonpeptide CCK-B antagonists: Design and development of quinazolinone derivatives as potent, selective, and orally active CCK-B antagonists" *J. Med. Chem.* 41:1042-1049 (1998).

Singh et al. "4-Quinazolones—II Synthesis of some imidazo [1,5-a] quinazolones" *J. Indian Chem. Soc.* 46(1):21-25 (1969).

Badawy et al. "Chemistry of Quinazolines: Reinvestigation of the Action of Hydrazine on Thioxo Derivatives" *J. Heterocyclic Chem.* 22: 1535-1536 (1985).

Yu et al. "Synthesis and x-ray crystallographic analysis of quinazolinone cholecystokinin/gastrin receptor ligands" *J. Med. Chem.* 35:2534-2542 (1992).

Zaher et al. "Reactions of 2-p-anisyl-3(4H), 1-benzoxazin-4-one with ammonia, primary amines, hydrazine, phenylhydrazine & Grignard reagents" *Indian J. Chem.* 12:1212-1215 (1974).

Kulkarni et al. "Possible antifertility agents. Part-I. Synthesis of 2-(N,N-substituted-aminomethyl)-3-(2-pyridyl)-4(3H)-oxo-3,1-quinazolined" *J. Indian Chem.* LXI:720-721 (1984).

Majo et al. "Dimerization of substituted 2-aminobenzoic acids under Vilsmeier conditions: A novel route to the synthesis of 4-(3H)-quinazolinones" *Tet. Lett.* 37(28):5015-5018 (1996).

Rathman et al. "Functionalization of 2-methyl-3-o-tolyt-4(3H)-quinazolinone and related compounds through carbanion reactions at the 2-methyl group" *J. Org. Chem.* 45:2169-2176 (1980).

Padia et al. "Design and synthesis of novel nonpeptide CCK-B receptor antagonists" *Bioorg. Med. Chem. Lett.* 7(7):805-810 (1997).

Zentmyer et al. "The so-called acylanthranils (3,1,4-benzoxazones). I. Preparation; reactions with water, ammonia, and aniline; structure" *J. Organic Chemistry*, 14: 967-981 (1949).

Panday, V.K. "Possible Antiparkinsonian Compounds Part XI: Synthesis of 2-aryl/alkyl-3-[β-(3'-4'-dihydroxyphenyl) ethyl]-quinazolin (3H)-4-one and 2-aryl/alkyl-3-[(7'-(phenothiazinyl)-ethyl]-quinazolin/(3H)-4-one" *Acta Ciencia Indica* 4(3):230-235 (1978).

Tiwari et al. Chemical Abstracts, vol. 96, Abstract No. 142790p (1982).

Fadda et al. "Reactions of a heterocyclic β-enaminoester: Synthesis of pyranopyrimidines and pyrano[3', 2', : 5,6]pyrimidino[2,3-c][1,4]benzoxazine ring system," *Indian J. Chemistry* 29B: 1020-1024 (1990).

Wagner "Synthesis and Biological Evaluation of Some Derivatives of Pyrido[3, 2-d]pyrimidine" *Acta Poloniae Pharmaceutica—Drug Research* 51(4-5): 359-363 (1994).

El-Sharief et al. "Oxidation of 3-aminoquinazolinones with lead tetraacetate. A novel synthesis of naphtho-fused azirino-pyrazolo and 1,4,5-oxadiazepino-quinazolinones" *J. Chem Research* (S): 205-208 (2002).

Chenard et al. "Quinazolin-4-one α-Amino-3-hydroxy-5-methyl-4-isoxazolepropionic Acid (AMPA) Receptor Antagonists: Structure-Activity Relationship of the C-2 Side Chain Tether", *J. Med. Chem* 44:1710-1717 (2001).

Garg et al. "Synthesis and anti-implantation activity of α-(2-aryl-3-ethyl-4-oxo (3H) quinazolinyl)-α-(substituted styryl)-cyclohexanone thiosemicarbazones" *Biol. Mem.* 14(2):180-186 (1988).

Singh et al. "Synthesis and pharmacological screening of some 2-aryl-3-(phenyl-aryl-hydrazonyl)-quinazolin (3H) 4-ones" *Indian Drugs* 28(2):70-74 (1990).

Ahmad et al. "Monoamine oxidase Inhibitory Activity of 4 (3H)-Quinazolinones of Dopamine" *Indian J. of Pharm. Sci.* 126-127 (1979).

Tiwari et al. "Possible Antifertility Compounds Part III: Synthesis of 2-Hippuryl-3-Aryl-Quinazolinones" *J. Chem. Soc. Pak.* 3(4):215-217 (1981).

Pandey, V.K. "Antiparkinsonism and CNS Activities of 2-aryl alkyl-3-(β-(3'-4'-dihydroxyphenyl) Ethyl)-quinazolin (3H) 4-ones" *Biol. Mem.* 11(2):213-215 (1985).

Szabó et al. "Uj kinazolonszarmazekok szintezise es ciklizalasa [1,4]oxazepino- es [1,4]diazepino [3,4-b]kinazolonkka" *Magyar Kemiai Folyoirat* 102(8):343-355 (1996) translated abstract.

Reddy et al. "A New Synthesis of 2-aryl-2H-Pyrazino[2,1-β]Quinazolin-3,6(1H,4H)-Diones" *Synthetic Communications* 21(2):173-181 (1991).

Szabó et al. "Potencialis CCK-antagonista kinazolon-szarmazekok szintezse" *Acta Pharm. Hungarica* 65:133-136 (1995) translated abstract.

Pandey et al. "Quinazolyl-thiazoles as CNS acting agents" *Acta Pharm.* 46:51-59 (1996).

Reddy et al. "4-Heteryl-β-lactams: A facile synthesis of 1-aryl-4-[isopropylideneamino/methyl-4(3H)-oxoquinazolin-2-yl] azetidin-2-ones" *Indian J. of Chem.* 38B:40-44 (1999).

Reddy et al. "Bisazaheterocycles: Part VII—Synthesis of novel bisquinazolinonyl β-lactans" *Ind. J. of Chem.* 41B:1946-1949 (2002).

Gyimesi-Forrás et al. "Az AGP-alapu folyadek-kromatografias allofazis aikalmazasa kinazolon szarmazekok enantiomerjeinek elvalasztasaban" *Acta Pharma. Hungarica* 73:5-12 (2003) translated abstract.

Reddy et al. "Synthesis of 2-quinazolinonyl Imidazolidinones" *Ind. J. of Chem.* 42B:393-396 (2003).

Gyimesi-Forrás et al. "Optical Resolution of a Series of Potential Cholecystokinin Antagonist 4(3H)-Quinazolone Derivatives by Chiral Liquid Chromatography on $\alpha_1$-Acid Glycoprotein Stationary Phase" *J. of Chromat. Sci.* 38:430-434 (2000).

Jiang et al. "A Salt Bridge between an N-terminal Coiled Coil of gp41 and an Antiviral Agent Targeted to the gp41 Core Is Important for Anti-HIV-1 Activity" *Biochem. and Biophys. Res. Communications* 270:153-157 (2000).

Hughes et al. "Quinazoline Antifolate Thymidylate Synthase Inhibitors: Alkyl, Substituted Alkyl, and Aryl Substituents in the C2 Position" *J. Med. Chem.* 33:3060-3067 (1990).

Hassanein et al. "Sythesis of 2-Substituted-10H-[1,2,4] triazino [6,1-b] quinazoline-10-ones and 8,13,14,16 tetrahydronaphtho [2',3',:3,4] [1,2,5] triazepino [7,1-b] quinazoline-8,13,16-triones with biological interest" *Al-Azhar Bull. Sci.* 8(2):417-434 (1997).

Szabó et al. "Nitrogen Bridgehead Compounds: Part 88 [1], Synthesis of 3H,7H-[1,4]Diazepino[3,4-b]quinazoline-3,7-diones" *J. Heterocyclic Chem.* 34(21):21-25 (1997).

Kokosi et al. "Nitrogen Bridgehead Compounds Part 90. An Efficient Versatile Synthesis of 1-Methyl-2-substituted 1,2,3,4-Tetrahydro-6H-Pyrazino[2,1-b]Quinazoline-3,6-Diones" *Heterocycles* 48(9):1851-1866 (1998).

El-Maghraby et al. "Synthesis of Glycylaminothiazoles" *Ind. J. Chem.* 12:1058-1059 (1974).

Hassan et al. "Synthesis and antimicrobial activity of some new N-aminoacyl derivatives of 2-amino-4-phenylthiazole" *Acta Pharm.* 47:159-166 (1997).

West, "Solid State Chemistry and it's Applications," Wiley, New York, 1988, pp. 358 & 365.

Office Action mailed May 7, 2001 for U.S. Appl. No. 09/699,047, filed Oct. 24, 2000.

Office Action mailed Apr. 24, 2002, for U.S. Appl. No. 09/699,047, filed Oct. 24, 2000.

Office Action mailed Feb. 6, 2002, for U.S. Appl. No. 09/724,644, filed Nov. 28, 2000.

Office Action mailed Oct. 21, 2002, for U.S. Appl. No. 09/724,644, filed Nov. 28, 2000.

Office Action mailed Feb. 6, 2002, for U.S. Appl. No. 09/724,712, filed Nov. 28, 2000.

Office Action mailed Apr. 9, 2002, for U.S. Appl. No. 09/724,713, filed Nov. 28, 2000.

Office Action mailed Oct. 21, 2002, for U.S. Appl. No. 09/724,713, filed Nov. 28, 2000.

Office Action mailed Mar. 22, 2002, for U.S. Appl. No. 09/724,897, filed Nov. 28, 2000.

Office Action mailed Dec. 17, 2002, for U.S. Appl. No. 09/724,897, filed Nov. 28, 2000.

Office Action mailed Jul. 11, 2003, for U.S. Appl. No. 09/724,897, filed Nov. 28, 2000.

Office Action mailed May 12, 2004, for U.S. Appl. No. 09/724,897, filed Nov. 28, 2000.
Office Action mailed Jul. 26, 2002, for U.S. Appl. No. 09/724,941, filed Nov. 28, 2000.
Office Action mailed Jan. 13, 2003, for U.S. Appl. No. 09/724,941, filed Nov. 28, 2000.
Office Action mailed Jan. 7, 2004, for U.S. Appl. No. 09/724,941, filed Nov. 28, 2000.
Office Action mailed Jul. 3, 2002, for U.S. Appl. No. 09/724,778, filed Nov. 28, 2000.
Office Action mailed Dec. 27, 2002, for U.S. Appl. No. 09/724,778, filed Nov. 28, 2000.
Office Action mailed Aug. 8, 2003, for U.S. Appl. No. 09/724,778, filed Nov. 28, 2000.
Office Action mailed Dec. 29, 2003, for U.S. Appl. No. 09/724,778, filed Nov. 28, 2000.
Office Action mailed Mar. 30, 2004, for U.S. Appl. No. 09/724,778, filed Nov. 28, 2000.
Office Action mailed Jun. 25, 2004, for U.S. Appl. No. 09/724,778, filed Nov. 28, 2000.
International Search Report mailed Feb. 22, 2001, for PCT Application No. PCT/US00/29585, filed Oct. 26, 2000.
Written Opinion mailed Sep. 21, 2001, for PCT Application No. PCT/US00/29585, filed Oct. 26, 2000.
International Preliminary Examination Report mailed Jan. 17, 2002, for PCT Application No. PCT/US00/29585, filed Oct. 26, 2000.
Office Action mailed Aug. 8, 2003, for U.S. Appl. No. 10/300,967, filed Nov. 20, 2002.
International Search Report mailed Feb. 7, 2003, for PCT Application No. PCT/US02/37410, filed Nov. 20, 2002.
Written Opinion mailed Sep. 9, 2003, for PCT Application No. PCT/US02/37410, filed Nov. 20, 2002.
International Preliminary Examination Report mailed Aug. 11, 2004, for PCT Application No. PCT/US02/37410, filed Nov. 20, 2002.
International Search Report mailed Oct. 31, 2001, for PCT Application No. PCT/US01/13901, filed Apr. 27, 2001.
International Search Report mailed Oct. 17, 2003, for PCT Application No. PCT/US03/18778, filed Jun. 12, 2003.
Office Action mailed Oct. 18, 2004, for U.S. Appl. No. 10/462,002, filed Jun. 12, 2003.
Written Opinion mailed Mar. 2, 2004, for PCT Application No. PCT/US03/18778, filed Jun. 12, 2003.
International Preliminary Examination Report mailed Sep. 8, 2004, for PCT Application No. PCT/US03/18778, filed Jun. 12, 2003.
International Search Report and Written Opinion mailed Dec. 6, 2004, for PCT Application No. PCT/US04/01279, filed Jan. 20, 2004.
International Search Report mailed Aug. 29, 2003, for PCT Application No. PCT/US03/14787, filed May 9, 2003.
Written Opinion mailed Jun. 10, 2004, for PCT Application No. PCT/US03/14787, filed May 9, 2003.
International Preliminary Examination Report mailed Nov. 16, 2004, for PCT Application No. PCT/US03/14787, filed May 9, 2003.
International Search Report mailed Jul. 16, 2004, for PCT Application No. PCT/US03/13627, filed May 2, 2003.
Office Action mailed Nov. 2, 2004, for U.S. Appl. No. 10/366,828, filed Feb. 14, 2003.
International Search Report mailed Aug. 12, 2003, for PCT Application No. PCT/US03/04713, filed Feb. 14, 2003.
Written Opinion mailed Jun. 24, 2004, for PCT Application No. PCT/US03/04713, filed Feb. 14, 2003.
International Preliminary Examination mailed Dec. 8, 2004, for PCT Application No. PCT/US03/04713, filed Feb. 14, 2003.
International Search Report mailed Jul. 9, 2004, for PCT Application No. PCT/US03/23319, filed Jul. 23, 2003.
International Preliminary Examination Report mailed Sep. 30, 2004, for PCT Application No. PCT/US03/23319, filed Jul. 23, 2003.
International Search Report mailed May 20, 2004, for PCT Application No. PCT/US03/26093, filed Aug. 20, 2003.
International Preliminary Examination Report mailed Aug. 5, 2004, for PCT Application No. PCT/US03/26093, filed Aug. 20, 2003.
Office Action mailed Jan. 4, 2005, for U.S. Appl. No. 10/444,283, filed May 22, 2003.
International Search Report mailed Dec. 18, 2003, for PCT Application No. PCT/US03/16500, filed May 22, 2003.
International Preliminary Examination Report mailed Jun. 23, 2004, for PCT Application No. PCT/US03/16500, filed May 22, 2003.
Bergnes et al., "Compounds, Compositions, and Methods," U.S. Appl. No. 10/980,627, filed Nov. 2, 2004.
Bergnes et al., "Compounds, Compositions, and Methods," U.S. Appl. No. 10/982,195, filed Nov. 5, 2004.
Bergnes, "Compounds, Compositions, and Methods," U.S. Appl. No. 11/005,629, filed Dec. 7, 2004.
Written Opinion mailed Sep. 24, 2004, for PCT Application No. PCT/US02/41309, filed Dec. 20, 2002.
International Search Report mailed Oct. 12, 2004, for PCT Application No. PCT/US03/30788, filed Sep. 30, 2003.
Office Action mailed Feb. 7, 2005, for U.S. Appl. No. 10/435,069, filed May 8, 2005.
International Preliminary Examination Report mailed Jan. 28, 2005, for PCT Application No. PCT/US03/30788, filed Sep. 30, 2003.
Office Action mailed Apr. 27, 2005, for U.S. Appl. No. 10/429,195, filed May 2, 2003.
International Preliminary Examination Report mailed May 9, 2005, for PCT Application No. PCT/US03/13627, filed May 2, 2003.
International Search Report and Written Opinion mailed Apr. 28, 2005, for PCT Application No. PCT/US04/36253, filed Nov. 2, 2004.
International Search Report and Written Opinion mailed Jun. 14, 2005, for PCT Application No. PCT/US04/36853, filed Nov. 5, 2004.
Sauter et al., CAPLUS Abstract No. 87:84931 (1977).
Uchida et al., CAPLUS Abstract No. 81:152142 (1974).
Yamada et al., CAPLUS Abstract No. 134:252363 (2001).
Matsuoka et al., CAPLUS Abstract No. 133:150920 (2000).
Nugent et al., CAPLUS Abstract No. 123:143921 (1995).
De Melo et al., CAPLUS Abstract No. 117:143023 (1992).
Irikura et al., CAPLUS Abstract No. 105:42834 (1986).
Kyorin Pharmaceutical Co., Ltd., CAPLUS Abstract No. 103:87901 (1985).
Shuto et al., CAPLUS Abstract No. 90:72134 (1979).
Katagiri et al., CAPLUS Abstract No. 100:51536 (1984).
Hegrand et al., CAPLUS Abstract No. 80:95873 (1974).
Witkop et al., CAPLUS Abstract No. 75:77191 (1971).
Office Action mailed Jun. 24, 2005, for U.S. Appl. No. 10/773,602, filed Feb. 6, 2004.
Office Action mailed Jul. 6, 2005, for U.S. Appl. No. 10/982,195, filed Nov. 5, 2004.
Gavezzotti "Are Crystal Structures Predictable" *Acc. Chem. Res.* 27:309-314 (1994).
Wolff (ed.) *Burger's Medicinal Chemistry and Drug Discovery*, 5th Edition vol. 1: *Principles and Practice*, John Wiley & Sons, New York, pp. 975-977 (1995).
Banker et al. (eds.) *Modern Pharmaceuticals Third Edition, Revised and Expanded*, Marcel Dekker, Inc., New York, pp. 451 & 596 (1996).
Coleman et al. "Inhibitors of the mitotic kinesin spindle protein" *Expert Opin. Ther. Patents* 14(12):1659-1667 (2004).
Li et al. "Discovery and development of antimitotic agents that inhibit tubulin polymerisation for the treatment of cancer" *Expert Opin. Ther. Patents* 12(11): 1663-1702 (2002).
Malik et al., "Compositions, Devices and Methods for Treating Cardiovascular Disease," U.S. Appl. No. 11/147,406, filed Jun. 7, 2005.
Notice of Allowance mailed Oct. 17, 2002, for U.S. Appl. No. 09/699,047, filed Oct. 24, 2000.
Notice of Allowance mailed Feb. 4, 2003, for U.S. Appl. No. 09/724,644, filed Nov. 28, 2000.
Notice of Allowance mailed Feb. 6, 2003, for U.S. Appl. No. 09/724,713, filed Nov. 28, 2000.
Notice of Allowance mailed Oct. 14, 2004, for U.S. Appl. No. 09/724,897, filed Nov. 28, 2000.

Notice of Allowance mailed Oct. 24, 2005, for U.S. Appl. No. 09/724,897, filed Nov. 28, 2000.

Notice of Allowance mailed Mar. 22, 2006, for U.S. Appl. No. 09/724,897, filed Nov. 28, 2000.

Notice of Allowance mailed Apr. 28, 2004, for U.S. Appl. No. 09/724,941, filed Nov. 28, 2000.

Notice of Allowance mailed Nov. 12, 2004, for U.S. Appl. No. 09/724,778, filed Nov. 28, 2000.

Notice of Allowance mailed Oct. 6, 2005, for U.S. Appl. No. 09/724,778, filed Nov. 28, 2000.

Office Action mailed May 25, 2006, for U.S. Appl. No. 09/724,778, filed Nov. 28, 2000.

Notice of Allowance mailed Dec. 11, 2003, for U.S. Appl. No. 10/300,967, filed Nov. 20, 2002.

Office Action mailed Apr. 4, 2005, for U.S. Appl. No. 10/366,828, filed Feb. 14, 2003.

Notice of Allowance mailed Jul. 26, 2005, for U.S. Appl. No. 10/366,828, filed Feb. 14, 2003.

Office Action mailed Apr. 12, 2006, for U.S. Appl. No. 10/312,323, filed Aug. 15, 2003.

"Cytokinetics Announces Clinical and Non-Clinical Data on Ispinesib to be Presented at the 2005 AACR-NCI-EORTC International Meeting-Data from Two Phase Ib Combination Trials to be Presented," *Press Release*, Cytokinetics, Inc., 3 pages, (Nov. 10, 2005).

"Cytokinetics Announces Clinical and Non-Clinical Results on Ispinesib at the 2005 AACR-NCI-EORTC International Meeting-Data from Two Phase Ib Combination Trials Presented," *Press Release*, Cytokinetics, Inc., 4 pages, (Nov. 17, 2005).

"Cytokinetics Announces Interim Phase II Breast Cancer data for Ispinesib to be presented at San Antonio Breast Cancer Symposium," *Press Release*, Cytokinetics, Inc., 3 pages, (Dec. 1, 2005).

"Cytokinetics Announces Presentation of Ispinesib data at San Antonio Breast Cancer Symposium- Anti-cancer Activity Supportive of Continuation of Phase II Clinical Trial," *Press Release*, Cytokinetics, Inc., 3 pages, (12/8/2005).

"Cytokinetics Reports Data for Ispinesib (SB-715992) in Platinum-Sensitive Non-Small Cell Lung Cancer-Drug Candidate Does No Demonstrate Sufficient Anti-Tumor Activity to Proceed to Sage 2 in the Phase II Clinical Trial Drug Candidate Demonstrates Disease Stabilization in 50% of Patients," *Press Release*, Cytokinetics, Inc., 5 pages, (Mar. 30, 2006).

"Cytokinetics and GlaxoSmithKline Announce Seven Presentations At The 2002 Annual Meeting Of The American Association for Cancer Research Broad Alliance to Generate First IND In 2002," *Press Release*, Cytokinetics, Inc., 4 pages, (Apr. 8, 2002).

"Cytokinetics Announces the Initiation of a Broad Phase II Clinical Trials Program In Oncology for SB-715992-Milestone Payment Triggered under Collaboration with GlaxoSmithKline," *Press Release*, Cytokinetics, Inc., 3 pages, (Jan. 14, 2004).

"Cytokinetics Publication in Cancer Research Demonstrates Anti-tumor Activity of a Kinesin Spindle Protein (KSP) Inhibitor in a Preclinical Model- Preclinical Proof of Concept Emerges from Company's Research Efforts," *Press Release*, Cytokinetics, Inc., 3 pages, (May 3, 2004).

"Cytokinetics Announces Phase I Results for SB-715992 to be Presented at the 2004 Annual Meeting Of The American Society of Clinical Oncology," *Press Release*, Cytokinetics, Inc., 2 pages, (Jun. 2, 2004).

"Cytokinetics Announces Phase I Results for the SB-715992 presented at the 2004 Annual Meeting Of The American Society of Clinical Oncology- Safety and Tolerability Profile of the SB-715992 Supports Initiation of Broad Phase II Program," *Press Release*, Cytokinetics, Inc., 3 pages, (Jun. 7, 2004).

"Cytokinetics Announces the Initiation of an Additional Phase II Clinical Trial for Lead Cancer Drug Candidate- Company Provides Update on Clinical Trials Program for SB-715992 and SB-743921," *Press Release*, Cytokinetics, Inc., 4 pages, (Dec. 16, 2004).

\* cited by examiner

SYNTHESES OF QUINAZOLINONES

CROSS-REFERENCE TO RELATED APPLICATIONS

This application is a divisional of application Ser. No. 10/366,828, filed Feb. 14, 2003, now U.S. Pat. No. 7,009,049 which claims the benefit of provisional U.S. Application Ser. Nos. 60/357,244, filed Feb. 15, 2002 and 60/380,746, filed May 14, 2002, each incorporated herein by reference.

FIELD OF THE INVENTION

This invention relates to the synthesis of certain quinazolinone derivatives that are inhibitors of the mitotic kinesin KSP and are useful in the treatment of cellular proliferative diseases, for example cancer, hyperplasias, restenosis, cardiac hypertrophy, immune disorders and inflammation.

BACKGROUND OF THE INVENTION

Interest in the medicinal chemistry of quinazoline derivatives was stimulated in the early 1950's with the elucidation of the structure of a quinazoline alkaloid, 3-[β-keto-gamma-(3-hydroxy-2-piperidyl)-propyl]-4-quinazolone, from an Asian plant known for its antimalarial properties. In a quest to find additional antimalarial agents, various substituted quinazolines have been synthesized. Of particular import was the synthesis of the derivative 2-methyl-3-o-tolyl-4-(3H)-quinazolinone. This compound, though ineffective against protozoa was found to be a potent hypnotic and is known by the name methaqualone.

The pharmacologic activity of quinazolinones and related compounds has been more thoroughly investigated since the introduction of methaqualone. Quinazolinones and derivatives thereof are now known to have a wide variety of biological properties including hypnotic, sedative, analgesic, anticonvulsant, antitussive and anti-inflammatory activities.

Quinazolinone derivatives for which specific biological uses have been described include 2-(substituted phenyl)-4-oxo-quinazolines with bronchodilator activity (U.S. Pat. No. 5,147,875). U.S. Pat. Nos. 3,723,432, 3,740,442, and 3,925,548 describe a class of 1-substituted-4-aryl-2(1H)quinazolinone derivatives useful as anti-inflammatory agents. European patent publication EP 0 056 637 B1 describes a class of 4(3H)-quinazolinone derivatives for the treatment of hypertension. European patent publication EP 0 884 319 A1 describes pharmaceutical compositions of quinazolin-4-one derivatives used to treat neurodegenerative, psychotropic, and drug and alcohol induced central and peripheral nervous system disorders.

Quinazolinones are among a growing number of therapeutic agents used to treat cell proliferative disorders, including cancer. For example, PCT WO 96/06616 describes a pharmaceutical composition containing a quinazolinone derivative to inhibit vascular smooth muscle cell proliferation. PCT WO 96/19224 uses this same quinazolinone derivative to inhibit mesengial cell proliferation. U.S. Pat. Nos. 4,981,856, 5,081,124 and 5,280,027 describe the use of quinazolinone derivatives to inhibit thymidylate synthase, the enzyme that catalyzes the methylation of deoxyuridine monophosphate to produce thymidine monophosphate, which is required for DNA synthesis. U.S. Pat. Nos. 5,747,498 and 5,773,476 describe quinazolinone derivatives used to treat cancers characterized by over-activity or inappropriate activity of tyrosine receptor kinases. U.S. Pat. No. 5,037,829 describes (1H-azol-1-ylmethyl) substituted quinazoline compositions to treat carcinomas that occur in epithelial cells. PCT WO 98/34613 describes a composition containing a quinazolinone derivative useful for attenuating neovascularization and for treating malignancies. U.S. Pat. No. 5,187,167 describes pharmaceutical compositions comprising quinazolin-4-one derivatives, which possess anti-tumor activity.

The synthesis of quinazolinones has been described, for example, by Ager et al., *J. Med. Chem.*, 20:379–386 (1977). Quinazolinones have been obtained by acid-catalyzed condensation of N-acylanthranilic acids with aromatic primary amines. Other processes for preparing quinazolinones are described in U.S. Pat. Nos. 5,783,577, 5,922,866 and 5,187,167.

Syntheses of the class of quinazolinones presently of interest have been reported in WO 01/30768 (incorporated herein by reference) and are shown in Reaction Schemes A and B (below).

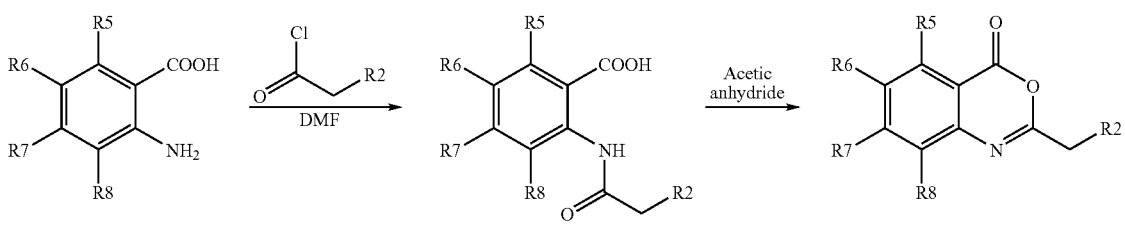

Reaction Scheme A

-continued

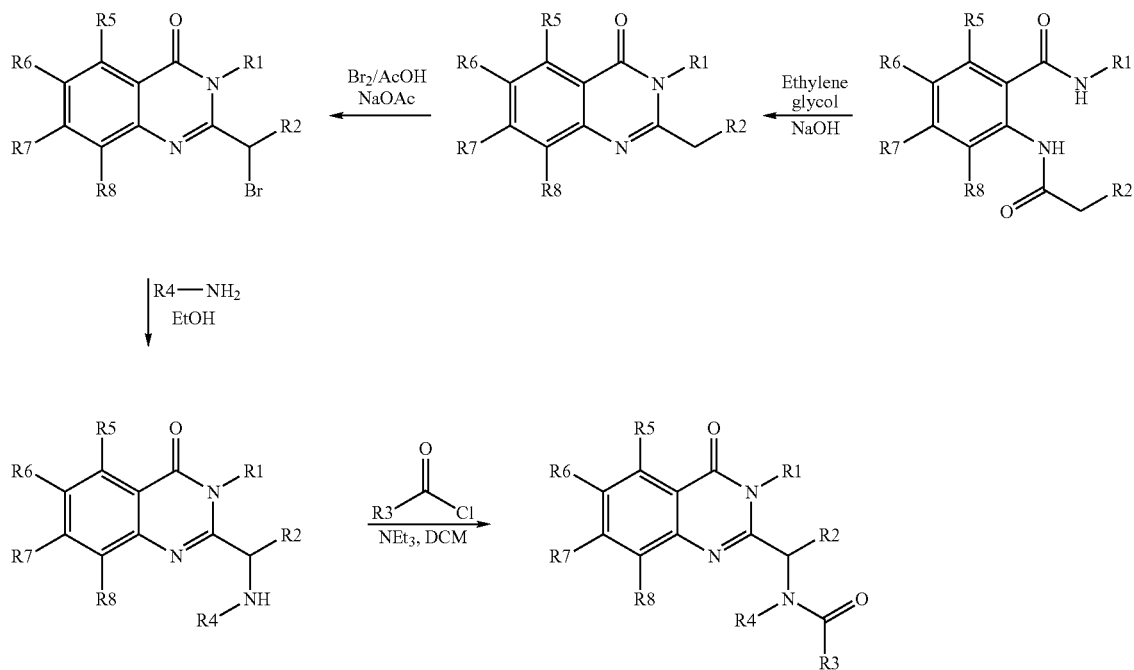

It has become particularly desirable to produce increased quantities of certain enantiomerically pure quinazolinones. It had previously been taught that such optically active (R)- and (S)-isomers can be prepared using chiral synthons or chiral reagents, or resolved using conventional techniques, for example: via formation of diastereoisomeric salts or complexes which can be separated, e.g., by crystallisation; via formation of diastereoisomeric derivatives which can be separated, e.g., by crystallisation, gas-liquid or liquid chromatography; via selective reaction of one enantiomer with an enantiomer-specific reagent, e.g., enzymatic oxidation or reduction, followed by separation of the modified and unmodified enantiomers; or via gas-liquid or liquid chromatography in a chiral environment, e.g., on a chiral support, such as silica with a bound chiral ligand or in the presence of a chiral solvent. Where the desired enantiomer is converted into another chemical entity by one of the separation procedures described above, a further step is described as potentially required to liberate the desired enantiomeric form. Alternatively, the asymmetric synthesis of specific enantiomers has been described using optically active reagents, substrates, catalysts or solvents, or by converting one enantiomer to the other by asymmetric transformation. An example of a prior synthesis from optically active starting materials is shown in Reaction Scheme B.

Reaction Scheme B

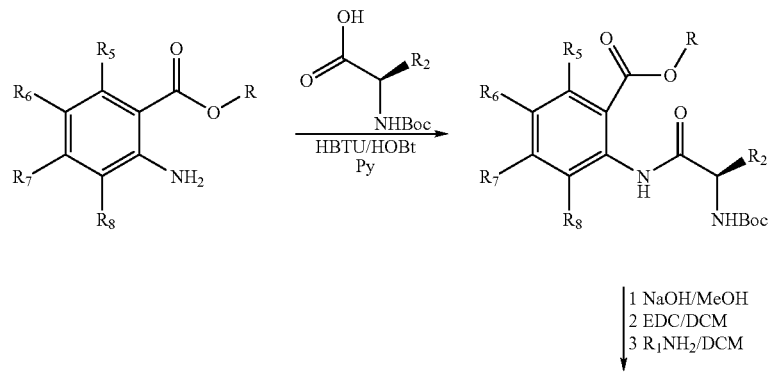

-continued

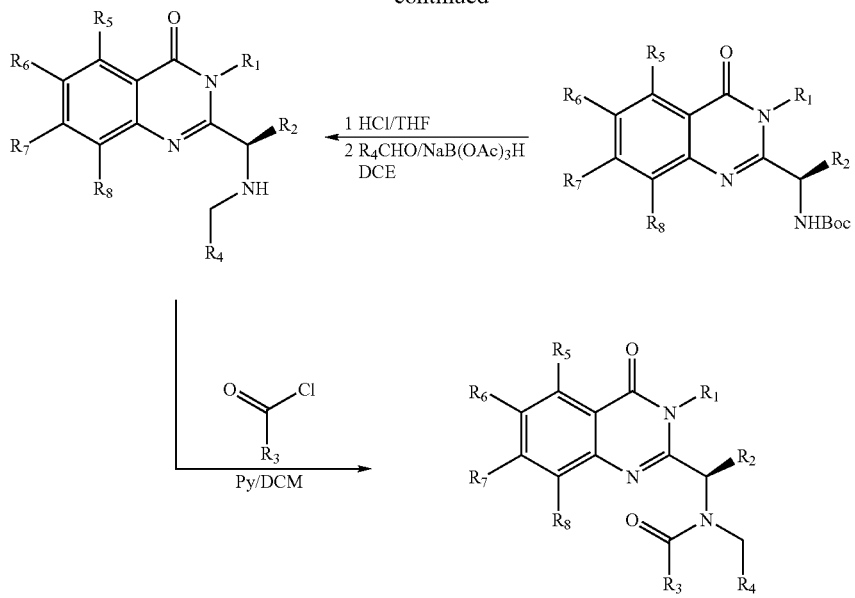

Notwithstanding such existing synthetic approaches, development of quinazolinones for new therapeutic indications has increased the need for producing these enantiomerically pure active agents. While effective for producing research quantities, the prior synthetic approaches are in many aspects too lengthy and uneconomical for production of larger scale batches of compound. Intermediate chemical resolutions require considerable time and result in relatively low yields. Moreover, certain reagents that are acceptable in small-scale syntheses (e.g., the use of bromine, sodium azide and triphenyl phosphine) are generally undesirable for large-scale production. Thus, there remains a need for improved quinzolinone syntheses, particularly for the larger scale production of enantiomerically pure quinazolinones

SUMMARY OF THE INVENTION

In accordance with the objects outlined above, the present invention provides intermediates, synthetic methods and novel quinazolinone compositions of matter, which can be used to treat diseases of proliferating cells.

In one aspect, the invention provides methods for the synthesis of enantiomerically pure quinazolinones employing the corresponding enantiomer of a naturally occurring or substituted, optionally N-protected amino acid as the starting material, especially a D-amino acid or N-protected-D-amino acid. In a preferred aspect, the amino acid is selected from: alanine, valine, leucine, isoleucine, phenylalanine, serine, threonine, cysteine, methionine, tryptophan, tyrosine, asparagine, glutamine, asparaginate, glutamate, lysine, arginine, histidine, phenylglycine and 2-aminobutyric acid, especially the D-forms, and can be substituted and/or N-protected. Particularly preferred are alanine, valine, leucine, isoleucine and 2-aminobutyric acid. More particularly preferred are D-alanine, D-valine, D-leucine, D-isoleucine, and D-2-aminobutyric acid and with these amino acids having an amine protecting group being even more preferred. Most preferred is N-Boc-D-valine or N-CBZ-D-valine.

In a related aspect, the invention provides a method for the synthesis of an enantiomerically pure quinazolinone via the use, as a starting material, of an enantiomerically pure compound of Formula 101:

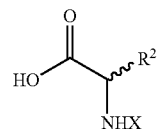

101 where:
R$^2$ is selected from: alkyl, oxaalkyl, aryl, alkylaryl, heteroaryl, alkylheteroaryl, substituted alkyl, substituted aryl, and substituted alkylaryl, substituted heteroaryl, and substituted alkylheteroaryl; and X is hydrogen or a protecting group (preferably selected from Boc, CBZ, phthalide, alloc, and teoc).

In a further related aspect, the method includes the steps of:

A) contacting a compound of Formula 101 with isobutyl chloroformate, and

B) contacting the product of step A with a compound of Formula 103:

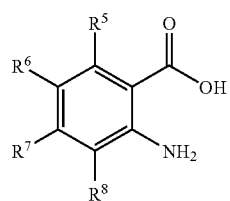

103 where $R^5$, $R^6$, $R^7$ and $R^8$ are independently chosen from hydrogen, alkyl, alkoxy, halogen, fluoroalkyl, nitro, cyano, substituted alkyl, dialkylamino, alkylsulfonyl, alkylsulfonamido, sulfonamidoalkyl, sulfonamidoaryl, alkylthio, carboxyalkyl, carboxamido, aminocarbonyl, aryl and heretoaryl.

Still another aspect of the invention provides a method for the synthesis, from the corresponding enantiomer of a naturally occurring or substituted, optionally N-protected amino acid (especially valine) as the starting material, of a compound represented by Formula I:

Formula I where:
- $R^1$ is chosen from hydrogen, alkyl, aryl, alkylaryl, heteroaryl, alkylheteroaryl, substituted alkyl, substituted aryl, substituted alkylaryl, substituted heteroaryl, and substituted alkylheteroaryl;
- $R^2$ is chosen from alkyl, oxaalkyl, aryl, alkylaryl, heteroaryl, alkylheteroaryl, substituted alkyl, substituted aryl, substituted alkylaryl, substituted heteroaryl, and substituted alkylheteroaryl;
- $R^3$ is chosen from hydrogen, alkyl, aryl, alkylaryl, heteroaryl, alkylheteroaryl, substituted alkyl, substituted aryl, substituted alkylaryl, substituted heteroaryl, substituted alkylheteroaryl, oxaalkyl, oxaalkylaryl, substituted oxaalkylaryl, $R^9O$— and $R^9$—NH—;
- $R^4$ is chosen from hydrogen, alkyl, aryl, alkylaryl, heteroaryl, alkylheteroaryl, substituted alkyl, substituted aryl, substituted alkylaryl, substituted heteroaryl, and substituted alkylheteroaryl;
- $R^5$, $R^6$, $R^7$ and $R^8$ are independently chosen from hydrogen, hydroxy, alkyl, alkoxy, halogen, fluoroalkyl, nitro, cyano, substituted alkyl, amino, alkylamino, dialkylamino, alkylsulfonyl, alkylsulfonamido, sulfonamidoalkyl, sulfonamidoaryl, alkylthio, carboxyalkyl, carboxamido, aminocarbonyl, aryl and heretoaryl; and
- $R^9$ is chosen from alkyl, aryl, alkylaryl, heteroaryl, alkylheteroaryl, substituted alkyl, substituted aryl, substituted alkylaryl, substituted heteroaryl, and substituted alkylheteroaryl.

In one of its preferred aspects, the methods, compositions and formulations of the present invention pertain to the (R)-enantiomer of a compound represented by Formula I where:
- $R^1$ is alkylaryl or substituted alkylaryl (preferably benzyl or substituted benzyl; most preferably benzyl);
- $R^2$ is lower alkyl (preferably ethyl, i-propyl, c-propyl, t-butyl or c-pentyl) or substituted lower alkyl (such as methylthiomethyl);
- $R^3$ is alkyl (preferably, methyl), substituted alkyl (preferably alkoxyalkyl such as methoxymethyl, or heterocycloalkyl such as N-morpholinomethyl), aryl (preferably phenyl), substituted aryl (preferably lower alkyl-, lower alkoxy-, and/or halo-substituted phenyl), alkylaryl (preferably benzyl and phenylvinyl), alkylheteroaryl, oxaalkylaryl (preferably phenoxy lower alkyl), oxaalkylheteroaryl, substituted alkylaryl (preferably substituted benzyl and substituted phenylvinyl), substituted alkylheteroaryl, substituted oxaalkylaryl (preferably substituted phenoxy lower alkyl), or substituted oxaalkylheteroaryl;
- $R^4$ is substituted alkyl (preferably a primary-, secondary- or tertiary-amino-substituted lower alkyl); and
- $R^5$, $R^6$, $R^7$ and $R^8$ are chosen from hydrogen, halo (preferably chloro and fluoro), lower alkyl (preferably methyl), substituted lower alkyl, lower alkoxy (preferably methoxy), alkylthio (preferably methylthio) and cyano.

In yet another of its aspects, the present invention provides a method for the synthesis of an enantiomerically pure compound of Formula 107/203:

107/203 where:
- $R^1$ is chosen from hydrogen, alkyl, aryl, alkylaryl, heteroaryl, alkylheteroaryl, substituted alkyl, substituted aryl, substituted alkylaryl, substituted heteroaryl, and substituted alkylheteroaryl;
- $R^2$ is chosen from alkyl, oxaalkyl, aryl, alkylaryl, heteroaryl, alkylheteroaryl, substituted alkyl, substituted aryl, and substituted alkylaryl, substituted heteroaryl, and substituted alkylheteroaryl;
- $R^5$, $R^6$, $R^7$ and $R^8$ are independently chosen from hydrogen, hydroxy, alkyl, alkoxy, halogen, fluoroalkyl, nitro, cyano, substituted alkyl, amino, alkylamino, dialkylamino, alkylsulfonyl, alkylsulfonamido, sulfonamidoalkyl, sulfonamidoaryl, alkylthio, carboxyalkyl, carboxamido, aminocarbonyl, aryl and heretoaryl; and
- X is hydrogen or a protecting group (preferably selected from Boc, CBZ, phthalide, alloc, and teoc), including the steps:
A) contacting isobutyl chloroformate with a compound of Formula 101:

101

B) contacting the product of step A with a compound of Formula 103:

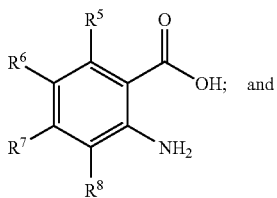

C) converting the product of step B to the compound of Formula 107/203.

In a preferred embodiment of this aspect of the invention $R^2$ is selected from ethyl, i-propyl, c-propyl, t-butyl or c-pentyl.

In another of its aspects, the present invention pertains to a composition of matter or pharmaceutical formulation including compound or pharmaceutically acceptable salt of Formula I and a detectable amount of one or more of the following:

A) a compound of Formula 101:

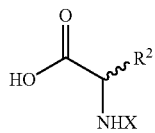

where X is hydrogen or a protecting group (preferably selected from Boc, CBZ, phthalide, alloc, and teoc);

B) a compound of Formula 103:

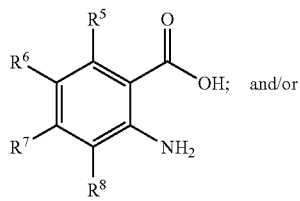

C) a cyclo-dehydration reagent employed in the synthesis thereof.

In a preferred embodiment of this aspect, the novel quinazolinone composition or pharmaceutical formulation contains a detectable quantity of naturally occurring or substituted, optionally N-protected amino acid, preferably a chiral amino acid (especially valine, preferably D-valine or an N-protected D-valine) and/or a detectable quantity of HMDS, lithium (or a lithium reagent) employed in synthesis of the quinazolinone.

DETAILED DESCRIPTION OF THE INVENTION

Definitions

As used in the present specification, the following words and phrases are generally intended to have the meanings as set forth below, except to the extent that the context in which they are used indicates otherwise.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl, " as defined below. It will be understood by those skilled in the art with respect to any group containing one or more substituents that such groups are not intended to introduce any substitution or substitution patterns that are sterically impractical and/or synthetically non-feasible.

Certain compound, reactant, or reaction parameter abbreviations are defined as follows:

Ac=acetyl
alloc=allyloxycarbonyl
Boc=t-butyloxy carbonyl
Bu=butyl
c-=cyclo
CBZ=carbobenzoxy=benzyloxycarbonyl
DCM=dichloromethane=methylene chloride=$CH_2Cl_2$
DMF=N,N-dimethylformamide
Et=ethyl
HMDS=hexamethyldisilazine
HOAc=acetic acid
IPA=isopropyl alcohol
Me=methyl
mesyl=methanesulfonyl
MTBE=methyl t-butyl ether
OAc=acetate
Ph=phenyl
PhOH=phenol
PTSA=para-toluenesulfonic acid
PyBroP=bromo-tris-pyrrolidino-phosphonium hexafluorophosphate
rt=room temperature
s-=secondary
t-=tertiary
teoc=2,2,2-trichloroethoxycarbonyl
TFA=trifluoroacetic acid
THF=tetrahydrofuran.

Alkyl is intended to include linear, branched, or cyclic hydrocarbon structures and combinations thereof. Lower alkyl refers to alkyl groups of from 1 to 5 carbon atoms. Examples of lower alkyl groups include methyl, ethyl, propyl, isopropyl, butyl, s-and t-butyl and the like. Preferred alkyl groups are those of $C_{20}$ or below. More preferred alkyl groups are those of $C_{13}$ or below. Cycloalkyl is a subset of alkyl and includes cyclic hydrocarbon groups of from 3 to 13 carbon atoms. Examples of cycloalkyl groups include c-propyl, c-butyl, c-pentyl, norbornyl, adamantyl and the like. In this application, alkyl refers to alkanyl, alkenyl and alkynyl residues; it is intended to include cyclohexylmethyl, vinyl, allyl, isoprenyl and the like. Alkylene refers to the same residues as alkyl, but having two points of attachment. Examples of alkylene include ethylene (—$CH_2CH_2$—), propylene (—$CH_2CH_2CH_2$—), dimethylpropylene (—$CH_2C(CH_3)_2CH_2$—) and cyclohexylpropylene (—$CH_2CH_2CH(C_6H_{13})$—). When an alkyl residue having a specific number of carbons is named, all geometric isomers having that number of carbons are intended to be encompassed; thus, for example, "butyl" is meant to include n-butyl, sec-butyl, isobutyl and t-butyl; "propyl" includes n-propyl and isopropyl.

Alkoxy or alkoxyl refers to groups of from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Lower-alkoxy refers to groups containing one to four carbons.

Acyl refers to groups of from 1 to 8 carbon atoms of a straight, branched or cyclic configuration, or a combination of any such configurations, attached to the parent structure through a carbonyl functionality. Such acyl groups can be saturated or unsaturated, and aromatic or non-aromatic. One or more carbons in the acyl residue can be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower-acyl refers to groups containing one to four carbons.

Aryl and heteroaryl mean a 5- or 6-membered aromatic or heteroaromatic ring containing 0–3 heteroatoms selected from O, N, or S; a bicyclic 9- or 10-membered aromatic or heteroaromatic ring system containing 0–3 heteroatoms selected from O, N, or S; or a tricyclic 13- or 14-membered aromatic or heteroaromatic ring system containing 0–3 heteroatoms selected from O, N, or S. The aromatic 6- to 14-membered carbocyclic rings include, e.g., benzene, naphthalene, indane, tetralin, and fluorene and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

Alkylaryl refers to a residue in which an aryl moiety is attached to the parent structure via an alkyl residue. Examples are benzyl, phenethyl, phenylvinyl, phenylallyl and the like. Oxaalkyl and oxaalkylaryl refer to alkyl and alkylaryl residues in which one or more methylenes have been replaced by oxygen. Examples of oxaalkyl and oxaalkylaryl residues are ethoxyethoxyethyl (3,6-dioxaoctyl), benzyloxymethyl and phenoxymethyl; in general, glycol ethers, such as polyethyleneglycol, are intended to be encompassed by this group. Alkylheteroaryl refers to a residue in which a heteroaryl moiety is attached to the parent structure via an alkyl residue. Examples include furanylmethyl, pyridinylmethyl, pyrimidinylethyl and the like.

Oxaalkyl and oxaalkylaryl refer to alkyl and alkylaryl residues in which one or more methylenes have been replaced by oxygen. Examples of oxaalkyl and oxaalkylaryl residues are ethoxyethoxyethyl (3,6-dioxaoctyl), benzyloxymethyl and phenoxymethyl; in general, glycol ethers, such as polyethyleneglycol, are intended to be encompassed by this group.

Alkylheteroaryl refers to a residue in which a heteroaryl moiety is attached to the parent structure via an alkyl residue. Examples include furanylmethyl, pyridinylmethyl, pyrimidinylethyl and the like.

Heterocycle means a cycloalkyl or aryl residue in which one to four of the carbons is replaced by a heteroatom such as oxygen, nitrogen or sulfur. Examples of heterocycles that fall within the scope of the invention include imidazoline, pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like. "N-heterocyclyl" refers to a nitrogen-containing heterocycle as a substituent residue. The term heterocyclyl encompasses heteroaryl, which is a subset of heterocyclyl. Examples of N-heterocyclyl residues include 4-morpholinyl, 4-thiomorpholinyl, 1-piperidinyl, 1-pyrrolidinyl, 3-thiazolidinyl, piperazinyl and 4-(3,4-dihydrobenzoxazinyl). Examples of substituted heterocyclyl include 4-methyl-1-piperazinyl and 4-benzyl-1-piperidinyl.

Substituted alkyl, aryl and heteroaryl refer to alkyl, aryl or heteroaryl wherein one or more hydrogen atom(s) is replaced with alkyl, halogen, hydroxy, alkoxy, alkylenedioxy (e.g. methylenedioxy) fluoroalkyl, carboxy (—COOH), carboalkoxy (i.e. acyloxy RCOO—), carboxyalkyl (—COOR), carboxamido, sulfonamidoalkyl, sulfonamidoaryl, aminocarbonyl, benzyloxycarbonylamino (CBZ-amino), cyano, carbonyl, nitro, dialkylamino, alkylamino, amino, alkylthio, alkylsulfinyl, alkylsulfonyl, alkylsulfonamido, arylthio, arylsulfinyl, arylsulfonyl, amidino, phenyl, benzyl, heteroaryl, heterocyclyl, substituted heterocyclyl, phenoxy, benzyloxy, or heteroaryloxy. For the purposes of the present invention, substituted alkyl also includes oxaalkyl residues, i.e. alkyl residues in which one or more carbons has been replaced by oxygen.

Halogen refers to fluorine, chlorine, bromine or iodine. Fluorine, chlorine and bromine are preferred. Dihaloaryl, dihaloalkyl, trihaloaryl etc. refer to aryl and alkyl substituted with a plurality of halogens, but not necessarily a plurality of the same halogen; thus 4-chloro-3-fluorophenyl is within the scope of dihaloaryl.

"Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The compounds described herein contain one or more asymmetric centers (e.g., the carbon to which $R_2$ is attached) and thus give rise to enantiomers, diastereomers, and other stereoisomeric forms that may be defined, in terms of absolute stereochemistry, as (R)- or (S)-. Most of the processes are described with regard to the presently preferred (R)-enantiomer, but are otherwise capable of producing all such possible isomers, e.g., the (S)-enantiomer. When the compounds described herein contain olefinic double bonds or other centers of geometric asymmetry, and unless specified otherwise, it is intended that the compounds include both E and Z geometric isomers. Likewise, except as otherwise specified, all tautomeric forms are also intended to be included. The term "enantiomerically pure" means having at least about 95% of the described enantiomer and preferably, at least about 97.5% enantiomeric excess.

SYNTHETIC PROCESSES OF THE INVENTION

The present invention provides intermediates, new and improved synthetic methods and novel quinazolinone compositions of matter, which can be used to treat diseases of proliferating cells. In one aspect, the invention provides methods for the synthesis of enantiomerically pure quinazolinones employing the corresponding enantiomer of amino acid precursors (particularly valine) as the starting material.

Initially, the present invention provides improvements upon previously disclosed methods for the synthesis of quinazolinones. For example, combining the first two steps illustrated in Reaction Scheme A via use of the same solvent (e.g., THF) for both steps and eliminating isolation of the intermediate product from Step 1 can afford a significant improvement in oxazolinone yield and overall efficiency. The ring opening, amination and re-cyclization of the third and fourth steps illustrated in Reaction Scheme A can also be combined (at the same time eliminating the use of chloroform), for example by employing toluene as the solvent and performing the re-cyclization at reflux. The bromination illustrated in Step 5 of Reaction Scheme A was observed to yield a sticky product requiring extended filtration times; this can be circumvented following the described water quenching by extracting the 2-(1'-bromoalkyl)-quinazolinone intermediate (e.g., in ethyl acetate).

The above-referenced 2-(1'-bromoalkyl)-quinazolinone is described as being converted to the corresponding 1'-amine via an azide intermediate, and then resolved (by recrystallization with tartaric acid) into S- and R-enantiomers, which are respectively used in lieu of the product produced by the first five steps shown in Reaction Scheme B. Yields in the second reaction illustrated in Reaction Scheme B can be improved by addition of a fourth substep, dehydration, for example employing LiOH (or another OH counter-ion such as K, Na, Cs, $Bu_4N$ or the like), ethylene glycol, and dioxane. The azide intermediate can also beneficially be extracted (e.g., with dichloromethane) instead of being isolated by filtration. The racemic 2-(1'-aminoalkyl)-quinazolinone can be beneficially isolated by crystallization (e.g., from ethyl acetate and MTBE) rather than chromatography, as can the resolved intermediate (from methanol). Coupling of the resolved amine with Boc-protected 3-aminopropanal can be effected by generating the aldehyde reactant and using it without isolation (in the solution in which it is produced) directly in the reductive amination. Isolation of the secondary amine (next to last step of Reaction Scheme B) can be performed by extractive work up (using aqueous NaOH). Finally, with regard to such prior processes, reducing the amounts of carbonyl chloride and the Hunnig's base (DIPEA) can eliminate the formation of undesired by-products (such as p-toluic acid) in the last step of Reaction Scheme B.

Also provided is a short and practical approach to a chiral quinazolinone amine intermediate (see Formula 107 in the Reaction Schemes). This can replace the seven steps leading to this intermediate in the route illustrated in Reaction Scheme A with basically one step, introducing the chiral center early via an aminoacid starting material, i.e., D-valine. This route offers additional advantages as it eliminates the need to carry out the operations or steps with the shortcomings described earlier (i.e. azide formation and reduction, classical resolution, etc.).

Synthetic Reaction Parameters

The terms "solvent", "inert organic solvent" or "inert solvent" mean a solvent inert under the conditions of the reaction being described in conjunction therewith. Solvents employed in synthesis of the compounds of the invention include, for example, methanol, acetone, water, acetonitrile, 1,4-dioxane, dimethylformamide, benzene, toluene, tetrahydrofuran, chloroform, methylene chloride (or dichloromethane), diethyl ether, pyridine and the like, as well as mixtures thereof. Unless specified to the contrary, the solvents used in the reactions of the present invention are inert organic solvents.

The term "q.s." means adding a quantity sufficient to achieve a stated function, e.g., to bring a solution to the desired volume (i.e., 100%).

Unless specified to the contrary, the reactions described herein take place at atmospheric pressure, generally within a temperature range from −10° C. to 110° C. Further, unless otherwise specified, the reaction times and conditions are intended to be approximate, e.g., taking place at about atmospheric pressure within a temperature range of about −10° C. to about 110° C. over a period of about 1 to about 24 hours.

The isolation and purification procedures described herein can be effected, if desired, by any suitable separation or purification procedure such as, for example, filtration, extraction, crystallization, column chromatography, thin-layer chromatography or preparative chromatography, or a combination of these procedures. Specific illustrations of suitable separation and isolation procedures can be had by reference to the examples hereinbelow. However, other equivalent separation or isolation procedures can, of course, also be used.

Starting Materials and Reactants

The compound NHBoc-protected D-valine, is commercially available, e.g., from Aldrich Chemical Company, Milwaukee, Wis. Other reactants are likewise commercially available or can be readily prepared by those skilled in the art using commonly employed methodology.

Brief Description of the Reaction Schemes

Reaction Scheme 1 illustrates the synthesis of a chiral [(quinazolin-2-yl)-2-substituted methylene]-carbamic acid tert-butyl ester from a corresponding NHBoc-protected D-amino acid.

Reaction Scheme 2 illustrates an alternative approach to substitution of the nitrogen at position 3 of a chiral [(quinazolin-2-yl)-2-substituted methylene]-carbamic acid tert-butyl ester.

Reaction Scheme 3 illustrates the de-protection, derivatization and amidation of the amino-methyl substituent of a [(quinazolin-2-yl)-2-substituted methylene]-carbamic acid tert-butyl ester.

Reaction Scheme 4 illustrates an alternative approach to derivatization of the nitrogen in an enantiomerically pure valine.

Reaction Scheme 5 illustrates an alternative approach to the synthesis of an N-protected [1-(4-oxo-3,4-dihydro-quinazolin-2-yl)-2-substituted methyl]-amine of Formula 107 from a 4-oxo-4H-benz[d][1,3]oxazin-2-yl compound of Formula 105.

While the structures in Reaction Schemes 1 to 5 are shown illustrating synthesis of an (R)-enantiomer, it should be understood that the underlying synthetic methodology is stereospecific and will produce the enantiomer corresponding to the configuration of the starting material.

Reaction Scheme 1

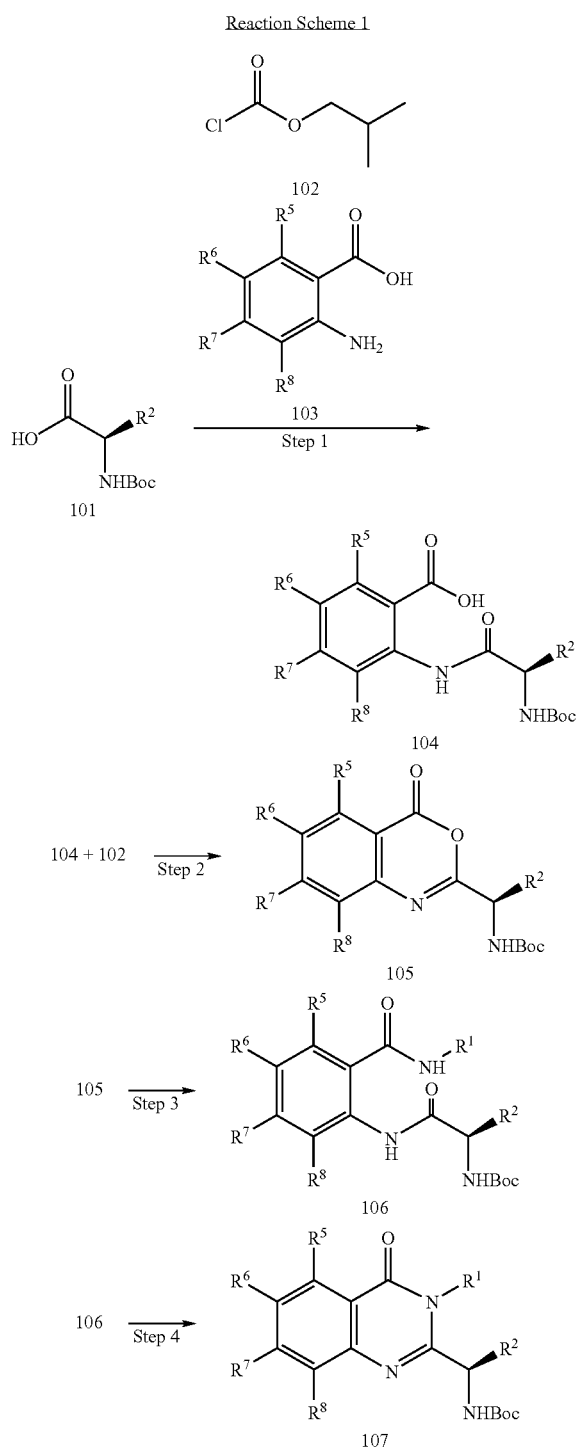

Referring to Reaction Scheme 1, Step 1, a compound of Formula 101 (e.g., an N-protected, chiral, naturally occuring or substituted amino acid such as valine; preferably N-Boc-D-valine) is converted to the corresponding 2-protected-carbonylamino-3-substituted methylamino optionally-substituted benzoic acid of Formula 104. Other naturally occurring and substituted α-amino acids can be employed as the compound of Formula 101, such as alanine, valine, leucine, isoleucine, phenylglycine, phenylalanine, serine, threonine, cysteine, methionine, tryptophan, tyrosine, asparagine, glutamine, asparaginate, glutamate, lysine, arginine, histidine and 2-aminobutyric acid; preferably alanine, valine, leucine, isoleucine, phenylglycine or 2-aminobutyric acid. Art-recognized N-protecting groups can be employed in the compound of Formula 101, including Boc, CBZ, phthalide, alloc, and teoc. The compound of Formula 101 is dissolved in an organic solvent (such as THF) in the presence of 1 to 2 molar equivalents of a base (such as N-methylmorpholine) and cooled to 0° C. Approximately 1 to 2 molar equivalents of isobutyl chloroformate (Formula 102) is slowly added (over a period of 5 to 30 minutes, preferably 15 minutes), preferably with stirring. The mixture is maintained at 0° C. and stirred for 1 to 2 hours (preferably 1.5 hours) to give the corresponding mixed anhydride (not shown). The mixed anhydride is carried forward without isolation or purification by the addition in one portion of an equimolar amount of an optionally substituted anthranilic acid [Formula 103, where $R^5$, $R^6$, $R^7$ and $R^8$ are independently chosen from hydrogen, alkyl, alkoxy, halogen, fluoroalkyl, nitro, cyano, substituted alkyl, dialkylamino, alkylsulfonyl, alkylsulfonamido, sulfonamidoalkyl, sulfonamidoaryl, alkylthio, carboxyalkyl, carboxamido, aminocarbonyl, aryl and heretoaryl; preferably hydrogen, halo (preferably chloro and fluoro), lower alkyl (preferably methyl), substituted lower alkyl, lower alkoxy (preferably methoxy), and cyano; most preferably hydrogen and one non-hydrogen substituent] followed by the addition of a second equimolar amount of the base (such as N-methylmorpholine). The reaction takes place at 0° C. over a period of 1 to 5 hours, preferably 3 hours, to give the corresponding compound of Formula 104 (which can also be carried forward without isolation or purification).

Referring to Reaction Scheme 1, Step 2, a 2-protected-carbonylamino-3-substituted methylamino optionally-substituted benzoic acid of Formula 104 is converted to the corresponding 4-oxo-4H-benz[d][1,3]oxazin-2-yl compound of Formula 105. An additional 1 to 2 molar equivalents of isobutyl chloroformate is added to the stirring benzoic acid of Formula 104 over a period of 5 to 60 minutes, preferably 30 minutes), along with the addition of 1 to 2 molar equivalents of a base (such as N-methylmorpholine). The reaction takes place at 0° C. over a period of 1 to 3 hours, preferably 2 hours, to give the corresponding compound of Formula 105 (which can also be carried forward without isolation or purification).

Referring to Reaction Scheme 1, Step 3, a 4-oxo-4H-benzo[d][1,3]oxazin-2-yl compound of Formula 105 is converted to the corresponding optionally substituted carbamoyl phenylamino compound of Formula 106. One to 3 molar equivalents of an amine (optionally substituted with a group selected from alkyl aryl, alkylaryl, heteroaryl, alkylheteroaryl, substituted alkyl, substituted aryl, substituted alkylaryl, substituted heteroaryl, and substituted alkylheteroaryl; preferably alkylaryl such as benzyl or substituted alkylaryl such as substituted benzyl; most preferably benzylamine) are added with continued stirring to a compound of Formula 105 in one or more portions over a period of 5 to 15 minutes (preferably 10 minutes) up to 10 hours (preferably in 2 or 3 portions each at 2 hour intervals). The reaction takes place at 0° C. to the corresponding compound of Formula 106 with a small amount of the corresponding compound of Formula 107. The two compounds are separated by conventional procedures (e.g., chromatography, extraction, washing, filtration, evaporation). An alternative approach overcoming racemization in the synthesis of the quinazolinone of Formula 107 is illustrated in Reaction Scheme 5 and its accompanying description. Notwithstanding such alternative approaches, the route illustrated in Reaction Scheme 1, Step 3 remains presently preferred both from the standpoints of safety and yield.

Referring to Reaction Scheme 1, Step 4, an optionally substituted carbamoyl phenylamino compound of Formula 106 is converted to the corresponding quinazolinone of Formula 107. The compound of Formula 106 is dissolved in an organic solvent (e.g., 1,4-dioxane/ethylene glycol 2:1 or dimethoxyethane), contacted with a slight to twice molar excess of a cyclo-dehydration reagent (stronger than NaOH pellets, e.g., lithium hydroxide monohydrate, HMDS, phosphorous oxychloride, oxalyl chloride, thionyl chloride, Burgess' reagent, $Ph_3P/I_2$, or a Vilsmeier reagent (DMF with phosphorous oxychloride, or DMF with thionyl chloride), preferably HMDS) and heated to reflux. The reaction takes place at reflux over a period of 3 to 36 hours (preferably 24 hours) followed by cooling and optionally acidification of the mixture to give a suspension of the corresponding quinazolinone of Formula 107, which is then isolated and purified by conventional procedures. Reaction time and work-up will depend on the cyclo-dehydration reagent that is employed.

Formula 201 is dissolved in an organic solvent (preferably THF) and contacted with a slight molar excess of a strong base (preferably lithium hydroxide monohydrate) to give the corresponding compound of Formula 202. The reaction takes place at reflux over a period of about 30 minutes to 2 hours, followed by cooling and acidification of the mixture to give a suspension, which is then isolated and purified via conventional procedures.

Referring to Reaction Scheme 2, Step 3, a quinazolinone of Formula 202 is converted to the corresponding 3-N-substituted quinazolinone of Formula 203. The compound of Formula 202 is dissolved in an organic solvent (e.g., DMF) and N-substituted via contact with halide of the desired substituent group (e.g., benzyl bromide) in the presence of an alkaline metal carbonate. The reaction takes place at room temperature over a period of 10 to 20 hours (preferably 16 hours) to give the corresponding compound of Formula 203, which is isolated and purified via conventional procedures (such as chromatography).

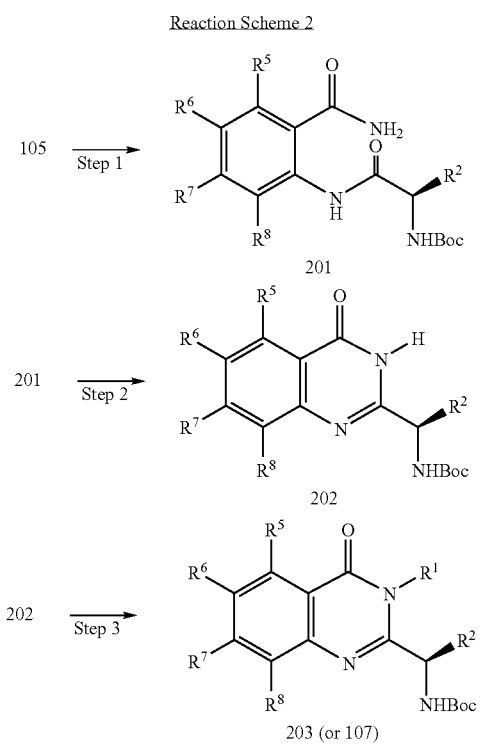

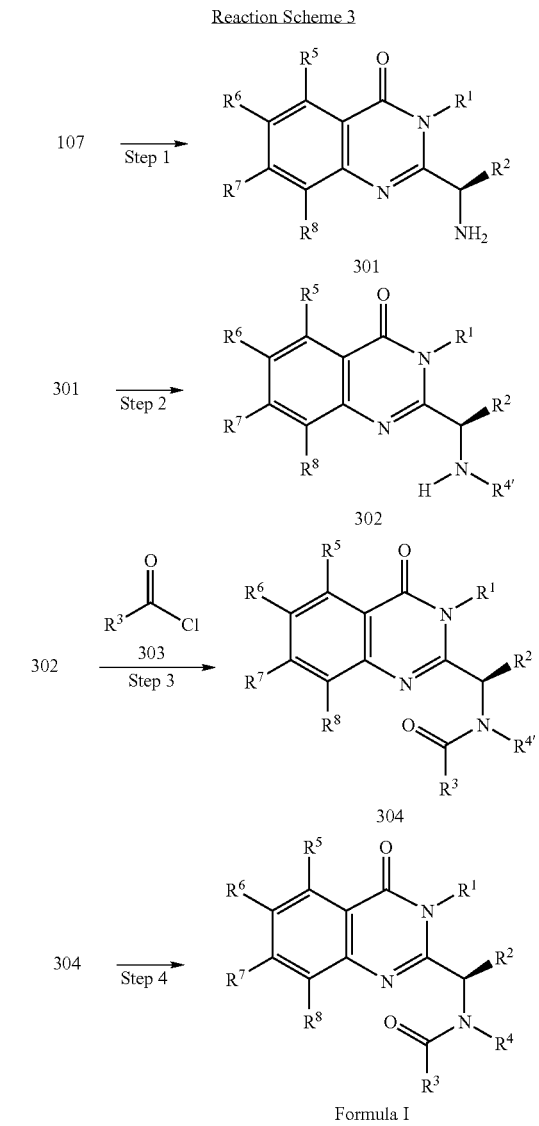

Referring to Reaction Scheme 2, Step 1, a 4-oxo-4H-benz[d][1,3]oxazin-2-yl compound of Formula 105 is converted to the corresponding carbamide of Formula 201. Gaseous ammonia is bubbled through a solution of the compound of Formula 105 (e.g., the stirring mixture obtained in Reaction Scheme 1, Step 2). The reaction takes place with stirring at 0° C. over a period of 1 to 3 hours (preferably 2 hours) followed by isolation and purification via conventional procedures.

Referring to Reaction Scheme 2, Step 2, a carbamide of Formula 201 is converted to the corresponding N-unsubstituted quinazolinone of Formula 202. The compound of Referring to Reaction Scheme 3, Step 1, an N-protected [1-(4-oxo-3,4-dihydro-quinazolin-2-yl)-2-substitutedmethyl]-amine of Formula 107 (where Boc is illustrated as the protecting group) is converted to the corresponding 2-(1-amino-2-substituted methyl)-3H-quinazolin-4-one compound of Formula 301. The compound of Formula 107 (or 203 or 503) is dissolved in an organic solvent (e.g., ethanol or toluene) and de-protected via addition of a strong, preferably anhydrous acid having a $pK_a \geq 1$ (e.g., PTSA or methanesulfonic acid). The reaction takes place (preferably avoiding the presence of water) at reflux over a period of 30 minutes to 2 hours (preferably 1 hour) followed by cooling, removal of the solvent and neutralization (e.g., by the addition of potassium bicarbonate or NaOH) and water to give the corresponding compound of Formula 301.

Referring to Reaction Scheme 3, Step 2, a 2-(1-amino-2-substituted methyl)-3H-quinazolin-4-one compound of Formula 301 is then converted to the corresponding 2-(1-substituted-amino-2-substituted methyl)-3H-quinazolin-4-one compound of Formula 302. The compound of Formula 301 is dissolved in an organic solvent (e.g., DCM) and contacted with a slight molar excess of a reducing reagent (such as sodium triacetoxyborohydride) followed by the portionwise addition of 1.4 molar equivalents of an $R^{4'}$-aldehyde (where $R^{4'}$ is selected from alkyl, aryl, alkylaryl, heteroaryl, alkylheteroaryl, substituted alkyl, substituted aryl, substituted alkylaryl, substituted heteroaryl, and substituted alkylheteroaryl; preferably substituted alkyl), most preferably a primary-, secondary- or tertiary-amino-substituted lower alkyl aldehyde having a protected amino group (NHBoc-aminopropanal, prepared via Swern oxidation and added directly in solution into the reductive amination step, being especially preferred). The reaction takes place at 10° C., over a period of 1 to 16 hours and is then quenched (e.g., by addition of a lower alkanol such as methanol) followed by stirring for an additional 25 minutes to 1 hour). The resulting mixture is washed under acidic and basic conditions and then isolated via conventional procedures.

Referring to Reaction Scheme 3, Step 3, a 2-(1-substituted-amino-2-substituted methyl)-3H-quinazolin-4-one of Formula 302 is then acylated to give the corresponding 2-(1-acyl-1-substituted-amino-2-substituted methyl)-3H-quinazolin-4-one of Formula 304. [It should be noted, for example in cases where $R^{4'}$ is a group of $R^4$ (e.g., not a $R^4$ precursor such as a protected amine) that the resulting compound of Formula 304 will also be a compound of Formula I.] The compound of Formula 302 is dissolved in an organic solvent (e.g., DCM) and contacted with 2 to 3.5 molar equivalents (preferably 2.2 molar equivalents) of DIPEA and stirred until dissolved. A slight molar excess of a carbonyl halide [such as Formula 303, where $R^3$ is alkyl, aryl, alkylaryl, heteroaryl, alkylheteroaryl, substituted alkyl, substituted aryl, substituted alkylaryl, substituted heteroaryl, substituted alkylheteroaryl, oxaalkyl, oxaalkylaryl, substituted oxaalkylaryl, $R^{15}O$— and $R^{15}$—NH—; $R^{15}$ being chosen from alkyl, aryl, alkylaryl, heteroaryl, alkylheteroaryl, substituted alkyl, substituted aryl, substituted alkylaryl, substituted heteroaryl, and substituted alkylheteroaryl; and $R^{16}$ being chosen from alkoxy, amino, alkylamino, dialkylamino, N-heterocyclyl and substituted N-heterocyclyl; $R^3$ preferably being alkyl, substituted alkyl (preferably alkoxyalkyl such as methoxymethyl), aryl (preferably phenyl), substituted aryl (preferably lower alkyl-, lower alkoxy-, and/or halo-substituted phenyl), alkylaryl (preferably benzyl and phenylviny), alkylheteroaryl, oxaalkylaryl (preferably phenoxy lower alkyl), oxaalkylheteroaryl, substituted alkylaryl (preferably substituted benzyl and substituted phenylvinyl), substituted alkylheteroaryl, substituted oxaalkylaryl (preferably substituted phenoxy lower alkyl), or substituted oxaalkylheteroaryl], most preferably p-toluoyl chloride (5.5 g, 4.7 mL, 1.1 eq) is added to the stirring solution and stirring continues for 4 to 10 hours (preferably 6 hours) after which the reaction is quenched (e.g., by addition of a lower alkanol such as methanol) and stirred for an additional 15 minutes to 1 hour (preferably 30 minutes). The resulting mixture is washed under acidic conditions and then isolated via conventional procedures (e.g., using a silica gel column).

Referring to Reaction Scheme 3, Step 4, a compound of Formula 304 (where $R^{4'}$ is a precursor to $R^4$) is then converted to the corresponding compound of Formula I. In a preferred synthesis, a compound of Formula 304 where $R^{4'}$ is N-Boc-aminopropyl is mixed with a large excess of TFA (premixed in an organic solvent, such as DCM). The reaction takes place, with stirring, at room temperature over 4 to 10 hours (preferably 6 hours), followed by cooling and addition of a strong base (e.g., 4N sodium hydroxide) until basic, isolation and purification via conventional procedures.

-continued

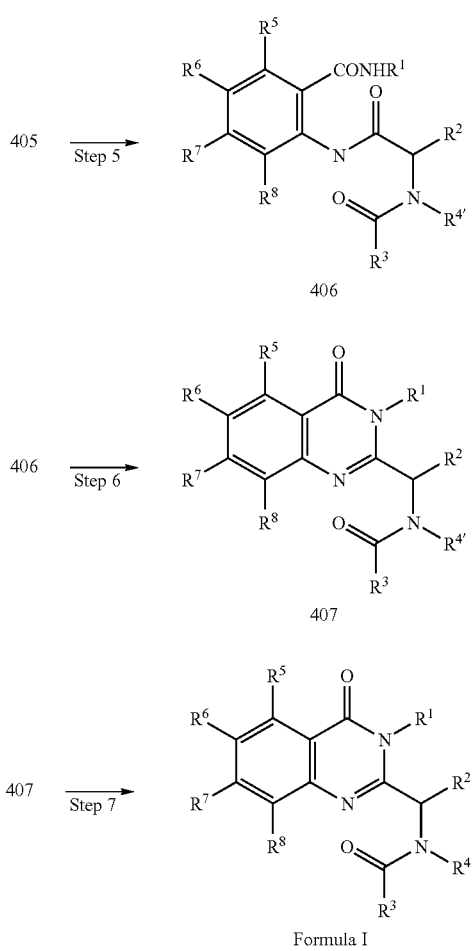

Formula I

The route illustrated in Reaction Scheme 4 incorporates the functionality on the primary amine even before the quinazolinone nucleus is constructed. This approach incorporates lower yield operations in early steps of the synthesis.

Referring to Reaction Scheme 4, Step 1, a solution of a 2-halo-3-substituted ethyl ester of Formula 401 in a lower alkanol (e.g., EtOH) is treated with a slight excess of a primary amine ($R^{4'}$—$NH_2$ where $R^{4'}$ is as described previously) and the mixture stirred at room temperature for 16 hours. Alternatively, an amino acid alkyl ester (such as valine ethyl ester) can be substituted for the compound of Formula 401. Reductive alkylation with an aldehyde (as shown above) results in the corresponding 2-amino-3-substituted ethyl ester of Formula 402 is isolated by conventional procedures.

Referring to Reaction Scheme 4, Step 2, a crude 2-amino-3-substituted ethyl ester of Formula 402 is dissolved in an organic solvent (e.g., dichloromethane) and treated with a slight excess of an $R^3$-acid chloride and a slight excess of triethylamine. The mixture is stirred at room temperature for 16 hours to afford the corresponding carboxamide of Formula 403, which is isolated and purified by conventional procedures.

Referring to Reaction Scheme 4, Step 3, a carboxamide of Formula 403 is dissolved in an organic solvent (e.g., THF) and then treated with a large excess (e.g., 6 eq) of aqueous LiOH. The mixture is stirred at room temperature for 16 hours overnight and then evaporated to dryness. The residue is triturated with dichloromethane, dried, filtered and evaporated to give the corresponding crude lithium salt. The lithium salt is dissolved in an organic solvent (e.g., DMF) and treated with an excess of PyBroP and a slight excess of an optionally substituted methyl anthranilate. The mixture is stirred at room temperature for 16 hours overnight to afford the corresponding carbonylamino-3-substituted methylamino optionally substituted benzoic acid methyl ester of Formula 404, which is isolated and purified by conventional procedures.

Referring to Reaction Scheme 4, Step 4, a methyl ester of Formula 404 is dissolved in an organic solvent (e.g., THF) and then treated with a large excess of aqueous LiOH. The mixture is stirred at room temperature for 16 hours overnight and then evaporated to dryness. The residue is triturated with dichloromethane, dried and isolated by conventional procedures to give the crude, lithium salt of the corresponding acid of Formula 405.

Referring to Reaction Scheme 4, Step 5, a lithium salt of Formula 405 is dissolved in an organic solvent (e.g., DMF) and treated with an excess of PyBroP and a slight excess of a primary amine ($R^1$—$NH_2$) in the presence of triethylamine. The mixture is stirred at room temperature for 16 hours to afford the corresponding bis-carboxamide of Formula 406, which is isolated and purified by conventional procedures.

Referring to Reaction Scheme 4, Step 6, a bis-carboxamide of Formula 406 is mixed with ethylene glycol to this is added a twice excess of a strong base (e.g., KOH). The mixture is stirred at 110° C. for 16 hours. After cooling to room temperature, the mixture is diluted with EtOAc and washed with $NaHCO_3$. The corresponding quinazolinone of Formula 407 is isolated and purified by conventional procedures Referring to Reaction Scheme 4, Step 7, quinazolinone of Formula 407 is converted to the corresponding compound of Formula I by procedures analogous to those described with reference to Reaction Scheme 3, Step 4.

Reaction Scheme 5

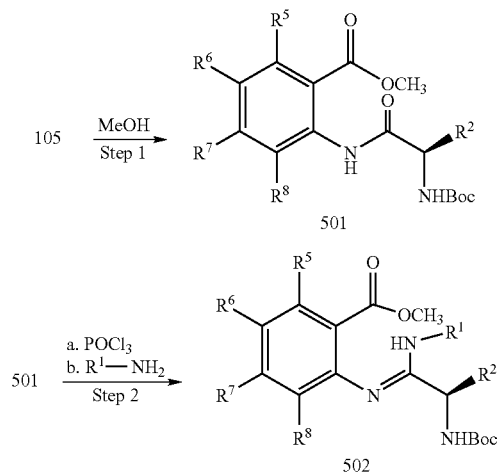

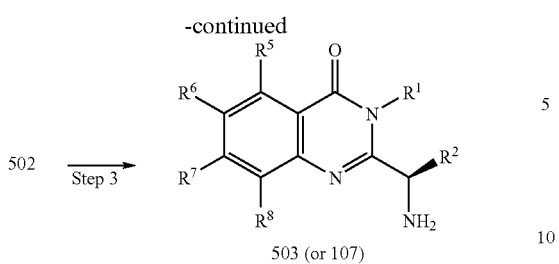

502 →Step 3→ 503 (or 107)

Referring to Reaction Scheme 5, Step 1, a benzoxazinone of Formula 105 is opened with methanol and converted to the corresponding ester of Formula 501. A 4-oxo-4H-benz[d][1,3]oxazin-2-yl compound of Formula 105 (prepared, for example, as described with reference to Reaction Scheme 1, Steps 1–2) is dissolved in methanol.

Referring to Reaction Scheme 5, Step 2, an ester of Formula 501 is converted to the corresponding amidine of Formula 502.

Referring to Reaction Scheme 5, Step 3, an amidine of Formula 502 is cyclized to afford the corresponding 4-oxo-4H-benz[d][1,3]oxazin-2-yl compound of Formula 503.

Novel Compositions of Matter

Compounds prepared by the above-described process of the invention and the products incorporating them (e.g., pharmaceutical formulations) can be identified by the presence of a detectable amount of certain novel starting materials and/or reactants, such as the starting amino acid (e.g., valine) or a reactant (e.g., a cyclo-dehydration agent such as LiOH or HMDS). While it is well known that pharmaceuticals must meet pharmacopoeia standards before approval and/or marketing, and that synthetic reagents (such as LiOH) or side products should not exceed the limits prescribed by pharmacopoeia standards, final compounds prepared by a process of the present invention may have minor, but detectable, amounts of such materials present, for example at levels in the range of 95% purity with no single impurity greater than 1%. These levels can be detected, e.g., by emission spectroscopy. It is important to monitor the purity of pharmaceutical compounds for the presence of such materials, which presence is additionally disclosed as a method of detecting use of a process of the invention.

The present invention provides a novel composition of matter or pharmaceutical formulation including a compound or pharmaceutically acceptable salt of Formula I and a detectable amount of one or more of the following:

A) a compound of Formula 101:

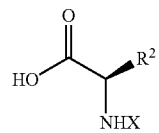

101 where X is a protecting group (preferably selected from Boc, CBZ, phthalide, alloc, and teoc);

B) a compound of Formula 103:

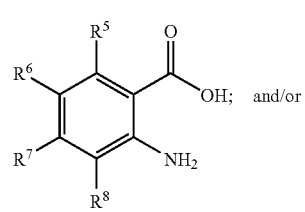

103

C) a cyclo-dehydration reagent (preferably HMDS, lithium (or a lithium reagent) employed in the synthesis thereof.

Preferred Processes and Last Steps

An enantiomerically pure quinazolinone is prepared via the use, as a starting material, of a compound of Formula 101:

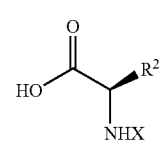

101 where:

R$^2$ is selected from: alkyl, oxaalkyl, aryl, alkylaryl, heteroaryl, alkylheteroaryl, substituted alkyl, substituted aryl, and substituted alkylaryl, substituted heteroaryl, and substituted alkylheteroaryl; and X is a protecting group (preferably selected from Boc, CBZ, phthalide, alloc, and teoc).

In a further preferred aspect, the process includes the steps of:

A) contacting a compound of Formula 101 with isobutyl chloroformate, and

B) contacting the product of step A with a compound of Formula 103:

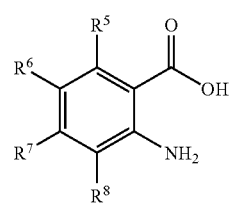

103 where R$^5$, R$^6$, R$^7$ and R$^8$ are independently chosen from hydrogen, alkyl, alkoxy, halogen, fluoroalkyl, nitro, cyano, substituted alkyl, dialkylamino, alkylsulfonyl, alkylsulfonamido, sulfonamidoalkyl, sulfonamidoaryl, alkylthio, carboxyalkyl, carboxamido, aminocarbonyl, aryl and heretoaryl.

An enantiomerically pure compound of Formula 107/203:

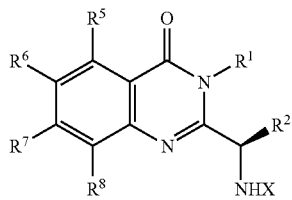

where:
R$^1$ is chosen from hydrogen, alkyl, aryl, alkylaryl, heteroaryl, alkylheteroaryl, substituted alkyl, substituted aryl, substituted alkylaryl, substituted heteroaryl, and substituted alkylheteroaryl;
R$^2$ is chosen from alkyl, oxaalkyl, aryl, alkylaryl, heteroaryl, alkylheteroaryl, substituted alkyl, substituted aryl, and substituted alkylaryl, substituted heteroaryl, and substituted alkylheteroaryl;
R$^5$, R$^6$, R$^7$ and R$^8$ are independently chosen from hydrogen, hydroxy, alkyl, alkoxy, halogen, fluoroalkyl, nitro, cyano, substituted alkyl, amino, alkylamino, dialkylamino, alkylsulfonyl, alkylsulfonamido, sulfonamidoalkyl, sulfonamidoaryl, alkylthio, carboxyalkyl, carboxamido, aminocarbonyl, aryl and heteroaryl; and
X is a protecting group (preferably selected from Boc, CBZ, phthalide, alloc, and teoc), is prepared by a process including the steps:
A) contacting isobutyl chloroformate with a compound of Formula 101:

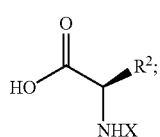

B) contacting the product of step A with a compound of Formula 103:

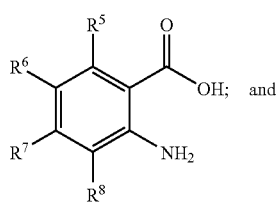

C) converting the product of step B to the compound of Formula 107/203.

In a preferred embodiment of this aspect of the invention R$^2$ is selected from ethyl, i-propyl, c-propyl, t-butyl or c-pentyl.

A compound of Formula I is contacted with a pharmaceutically acceptable acid, preferably methane sulfonic acid, to form the corresponding acid addition salt.

A pharmaceutically acceptable acid addition salt of Formula I is contacted with a base to form the corresponding free base of Formula I.

UTILITY AND ADMINISTRATION

The compositions made by the invention find use in a variety of applications, for example, as described in WO 01/30768 (previously incorporated by reference). As will be appreciated by those in the art, mitosis can be altered in a variety of ways; that is, one can affect mitosis either by increasing or decreasing the activity of a component in the mitotic pathway. Stated differently, mitosis can be affected (e.g., disrupted) by disturbing equilibrium, either by inhibiting or activating certain components. Similar approaches can be used to alter meiosis.

In a preferred use, the compositions made in the present invention are used to modulate mitotic spindle formation, thus causing prolonged cell cycle arrest in mitosis. By "modulate" herein is meant altering mitotic spindle formation, including increasing and decreasing spindle formation. By "mitotic spindle formation" herein is meant organization of microtubules into bipolar structures by mitotic kinesins. By "mitotic spindle dysfunction" herein is meant mitotic arrest and monopolar spindle formation.

The compositions made according to the invention are useful to bind to and/or modulate the activity of a mitotic kinesin, KSP. In a preferred embodiment, the KSP is human KSP, although KSP kinesins from other organisms can also be used. In this context, modulate means either increasing or decreasing spindle pole separation, causing malformation, i.e., splaying, of mitotic spindle poles, or otherwise causing morphological perturbation of the mitotic spindle. Also included within the definition of KSP for these purposes are variants and/or fragments of KSP. See WO 01/31335 "Methods of Screening for Modulators of Cell Proliferation and Methods of Diagnosing Cell Proliferation States", hereby incorporated by reference in its entirety. In addition, other mitotic kinesins can be used as binding targets for the compositions made in the present invention.

Anti-mitotic agents prepared according to the invention can be administered in a physiologically acceptable carrier to a patent, as described herein. Depending upon the manner of introduction, the compounds can be formulated in a variety of ways as discussed below. The concentration of therapeutically active compound in the formulation may vary from about 0.1–100 wt. %. The agents can be administered alone or in combination with other treatments, i.e., radiation, or other chemotherapeutic agents.

Pharmaceutical formulations employ the compositions made according to the invention typically in a water soluble form, such as pharmaceutically acceptable salts, which is meant to include both acid and base addition salts.

"Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents. The pharmaceutical compositions can also include one or more of the following: carrier proteins such as serum albumin; buffers; fillers such as microcrystalline cellulose, lactose, corn and other starches; binding agents; sweeteners and other flavoring agents; coloring agents; and polyethylene glycol. Additives are well known in the art, and are used in a variety of formulations.

The administration of the mitotic agents prepared according to the present invention can be done in a variety of ways as discussed above, including, but not limited to, orally, subcutaneously, intravenously, intranasally, transdermally, intraperitoneally, intramuscularly, intrapulmonary, vaginally, rectally, or intraocularly. In some instances, for example, in the treatment of wounds and inflammation, the anti-mitotic agents can be directly applied as a solution or spray.

EXAMPLES

The following examples are given to enable those skilled in the art to more clearly understand and to practice the present invention. They should not be considered as limiting the scope of the invention, but merely as being illustrative and representative thereof. The syntheses reported in Examples 1 through 4.1 were performed in the laboratories of IRIX Pharmaceuticals, Inc. (Florence, S.C.).

Example 1

Synthesis of (R)-N-(3-Amino-propyl)-N-[1-(3-benzyl-7-chloro-4-oxo-3,4-dihydro-quinalolin-2-yl)-2-methyl-propyl]-4-methyl-benzamide 1.1 7-Chloro-2-isobutyl-benzo[d][1,3]oxazin-4-one A dry 3-necked, round bottomed flask, equipped with an overhead stirrer, thermometer, dropping funnel, cooling bath and condenser was charged with 406.41 g of 2-amino-4-chlorobenzoic acid (1 eq.), 270 g (1.35 eq.) of sodium bicarbonate, $Na_2SO_4$ (as a dehydrating agent) and 1,000 mL of THF. After commencing agitation, 354.7 g (1.2 eq.) of isovaleryl chloride was added dropwise. The reaction was exothermic and generated a gas ($CO_2$). Temperature was maintained around 20–30° C. and completion of the reaction monitored by TLC (EtOAc/hexanes 1:1). The reaction mixture was then filtered and washed with THF (1,000 mL) the majority of which was then stripped off under vacuum. Acetic anhydride (1,450 mL) was then added to the reaction vessel and the temperature raised to 90–100° C. Completion of the reaction monitored by TLC (EtOAc/hexanes 1:1). The acetic anhydride was removed under vacuum at 80–100° C., followed by cooling to 60° C. The reaction vessel was then charged with heptane (1,000 mL) and cooled to 0° C. with stirring. The resulting precipitate was isolated by filtration and then washed with heptane (300 mL) and dried in a vacuum oven at 30° C. overnight to afford the title product (507 g, 90% yield).

1.2
3-Benzyl-7-chloro-2-isobutyl-3H-quinazolin-4-one

A flask, equipped with an overhead stirrer, heating mantle, condenser and Dean-Stark apparatus was charged with 1,500 mL of toluene, 412.7 g (1 eq.) of 7-chloro-2-isobutyl-benzo[d][1,3]oxazin-4-one and 281.0 g (1.5 eq.) of benzylamine and brought to reflux for 3 hours. After removal of the water, ethylene glycol (150 mL) and 14.2 g (0.2 eq.) of NaOH were added and the mixture was heated to 115° C. for 5 hours. Completion of the reaction was monitored by TLC, after which the temperature was cooled to 60° C. and the pH adjusted to about 7 with 1N HCl, followed by the addition of 1 L of brine. The top organic layer was separated and the aqueous layer extracted with methylene chloride (2×300 mL). The organic phases were combined and dried over sodium sulfate. Solvents were stripped off leaving a viscous oil to which warm hexane (500 mL) was added. The mixture was cooled in an ice bath to give White crystals, which were separated by filtration. The filter cake was washed with cold hexane (800 mL) and air dried to give the title product as a white solid (470 g). An additional 42.4 g of title product was obtained from the mother liquor (512.4 g, 90.3%).

1.3 3-Benzyl-2-(1-bromo-2-methyl)propyl-7-chloro-3H-quinazolin-4-one

A dry 3-necked, round bottomed flask, equipped with an overhead stirrer, thermometer, heating mantle, condenser and addition funnel was charged with 445 g (1 eq.) of 3-benzyl-7-chloro-2-isobutyl-3H-quinazolin-4-one, 158 g of sodium acetate and 1,300 mL of acetic acid. Temperature was raised to 30° C. followed by the addition of 230 g (1.1 eq.) bromine/AcOH over a period of about 2.5 hours. Completion of the reaction was monitored by TLC (temperature being increased to 50° C. until all unreacted starting material is consumed). After cooling to room temperature, the reaction mixture is poured into 8 L of cold water and agitated for 1 hour followed by extraction with ethyl acetate. The combined organic layers are washed with saturated, aqueous sodium bicarbonate, dried with $Na_2SO_4$ and the solvents removed under reduced pressure at 30° C. Drying overnight in a vacuum oven at 30° C. afforded the title product (536 g, 97%) as a white solid.

1.4 2-(1-Azido-2-methyl)propyl-3-benzyl-7-chloro-3H-quinazolin-4-one

A round bottomed flask, equipped with an overhead stirrer, thermometer, heating mantle and condenser was charged with 98 g (1.5 eq.) of sodium azide and 1,500 ML of DMF followed by the portionwise addition of 407 g (1 eq.) of 3-benzyl-2-(1-bromo-2-methyl)propyl-7-chloro-3H-quinazolin-4-one over 30 minutes. Temperature is increased to 40° C. and agitation continued for 4–5 hours. Upon completion of the reaction (monitored by TLC) the mixture is cooled to room temperature, poured into 6 L of water, 2 L of methylene chloride and 2 L of brine, and agitated. The bottom, organic phase is separated and the aqueous layer extracted with methylene chloride (1.2 L), dried over sodium sulfate, and the solvent stripped off leaving a warm viscous oil to which is added 0.5 L of warm hexane. Cooling on an ice bath gave a solid that was filtered and washed with 0.5 L of cold hexane. The filter cake was dried in a vacuum desiccator overnight to afford the title compound (319 g, 86.9%) as a white solid. (The filtrates can be stripped and triturated in MTBE for a second crop.)

1.5 2-(1-Amino-2-methyl)propyl-3-benzyl-7-chloro-3H-quinazolin-4-one

A dry 3-necked, round bottomed flask, equipped with an overhead stirrer, thermometer, condenser and nitrogen line was charged with 708 g of triphenylphosphine and 5,000 mL of THF resulting in a slight exotherm; followed by the portionwise addition of 945 g of 2-(1-azido-2-methyl)propyl-3-benzyl-7-chloro-3H-quinazolin-4-one over a period of about 15 minutes, followed by agitation for an additional 5 minutes. Temperature was maintained at about 20° C., using an ice cooling bath to maintain temperature during the exothermic addition of 1,400 mL of 2N aqueous HCl over a period of about 30 minutes. The solvent was stripped off under reduced pressure leaving a mixture of heavy yellow oil and water, which was dissolved in 4 L of ethyl acetate and dried with $Na_2SO_4$. After filtration, 5 L of MTBE was slowly added resulting in a precipitate that was filtered and dried at 40° C. under vacuum to give the hydrochloride salt of the title product (684 g, 78%) as a white solid. (The filtrates from re-crystallization can be reworked to obtain additional product.)

A portion (50 g) of the hydrochloride salt thus obtained was treated with 500 mL of saturated sodium bicarbonate and 100 mL of brine. After extraction with methylene chloride (2×250 mL) the bottom solution was separated, dried over $Na_2SO_4$ and the solvent was removed to afford the free amine (36 g) as a thick off-white oil.

1.6 R-2-(1-Amino-2-methyl)propyl-3-benzyl-7-chloro-3H-quinazolin-4-one

A round bottomed flask, equipped with an overhead stirrer, thermometer, and heating mantle, 2-(1-Amino-2-methyl)propyl-3-benzyl-7-chloro-3H-quinazolin-4-one (1,250 g) was dissolved in 8.7 L of IPA and warmed to 60° C. In a separate flask, 1,300 g of dibenzoyl-D-tartaric acid is dissolved in 8.3 L of warm isopropyl alcohol, and then quickly added to the warm amine solution under agitation. Crystallization began after about 1 minute, and the mixture was left overnight to cool under agitation to room temperature, yielding a white solid that was isolated by filtration. (Filtrates from this first recrystallization contained mostly the S-isomer.)

A 60 L reactor was charged with the crude wet material from the above-described crystallization and 22 L of methanol. Temperature was increased to 64° C. (reflux) dissolving the filtrate, followed by the addition of 30 L of hot isopropyl alcohol (quickly and under agitation). The heat was turned off and the solution allowed to cool overnight under agitation; crystallization began at 61.5° C., leaving a fine white suspension that was isolated by filtration (removing the mother liquor to the extent possible). The filter cake was washed with 3 L of isopropyl alcohol and then dried in a vacuum oven at about 35° C. overnight to afford the title compound (804 g, 31%) as a white fluffy solid. (Filtrates from this second crystallization can be stripped and recyrstallized using the same method to obtain a second crop of the desired R-isomer.)

1.7 (R)-{3-[1-(3-benzyl-7-chloro-4-oxo-3,4-dihydro-quinazolin-2-yl)-2-methyl-propylamino]-propyl}-carbamic acid tert-butyl ester.

A dry 3-necked, round bottomed flask, equipped with a magnetic stirrer, nitrogen inlet and cold bath was charged with 10.0 g of 2-(1-amino-2-methyl-propyl)-3-benzyl-7-chloro-3H-quinazolin-4-one (a compound of Formula 301 prepared, e.g., as described in Example 1.6 or 3.1), 50 mL of DCM and 6.20 g (1.2 eq) of sodium triacetoxyborohydride and cooled to 10° C., followed by the portionwise addition of N-Boc-3-aminopropanal 7.1 g (1.4 eq). Upon indication of completion by TLC, the reaction was quenched with 2.0 mL of methanol and stirred for an additional 30 minutes, during which a slight exotherm was observed. The mixture was washed with 1N hydrochloric acid (until the aqueous layer was clear and acidic)(also exothermic) and then washed with 2N sodium hydroxide (until basic), followed by drying over sodium sulfate, and filtration. The resulting off-white foam solid was filtered and solvents partially stripped under vacuum to give 16.0 g (110% yield) of the title compound of Formula 302, {3-[1-(3-benzyl-7-chloro-4-oxo-3,4-dihydro-quinazolin-2-yl)-2-methyl-propylamino]-propyl}-carbamic acid tert-butyl ester.

1.8 (R)-{3-[[1-(3-benzyl-7-chloro-4-oxo-3,4-dihydro-quinazolin-2-yl)-2-methyl-propyl]-(4-methyl-benzoyl)-amino]-propyl}-carbamic acid tert-butyl ester A dry 3-necked, round bottomed flask, equipped with a magnetic stirrer, nitrogen inlet and cold bath was charged with 16.0 g of {3-[1-(3-benzyl-7-chloro-4-oxo-3,4-dihydro-quinazolin-2-yl)-2-methyl-propylamino]-propyl}carbamic acid tert-butyl ester (the compound of Formula 302 prepared, e.g., as described in Example 1.7 or 3.2), 80 mL of DCM and 9.1 g (12 mL) (2.2 eq) of DIPEA and stirred until dissolved. To the stirring solution, p-toluoyl chloride 5.5 g (4.7 mL) (1.1 eq) was added and stirring continued for approximately 6 hours until the reaction was determined to be completed by TLC (hexanes/ethyl acetate 1:1). The reaction was quenched with methanol (5 mL) and stirred for an additional 30 minutes, then cooled followed by addition of 1N hydrochloric acid (exothermic) to wash until acidic. The resulting solution was dried over sodium sulfate, the solvents stripped under vacuum at 30–40° C. The crude product thus obtained was purified on a silica gel column (eluted with 15% ethyl acetate in hexanes) and concentrated to give the title compound of Formula 304 {3-[[1-(3-benzyl-7-chloro-4-oxo-3,4-dihydro-quinazolin-2-yl)-2-methyl-propyl]-(4-methyl-benzoyl)-amino]-propyl}-carbamic acid tert-butyl ester as an off-white foam solid, 10.8 g (60% yield).

1.9 (R)-N-(3-amino-propyl)-N-[1-(3-benzyl-7-chloro-4-oxo-3,4-dihydro-quinazolin-2-yl)-2-methyl-propyl]-4-methyl-benzamide A dry 3-necked, round bottomed flask, equipped with a magnetic stirrer, nitrogen inlet and cold bath was charged with 400.0 g of {3-[[1-(3-benzyl-7-chloro-4-oxo-3,4-dihydro-quinzolin-2-yl)-2-methyl-propyl]-(4-methyl-benzoyl)-amino]-propyl}-carbamic acid tert-butyl ester (the compound of Formula 304 prepared, e.g., as described in Example 1.8 or 3.3) and 1500 g of TFA (20 eq) premixed in DCM (6000 g). The mixture was stirred at room temperature for about 6 hours at which time the reaction was determined to be complete by TLC. The reaction vessel was cooled and slowly charged with 4N sodium hydroxide until basic. The resulting solution was washed with brine, dried over sodium sulfate and concentrated under reduced pressure at 35° C. to give the title compound of Formula I, (R)-N-(3-amino-propyl)-N-[1-(3-benzyl-7-chloro-4-oxo-3,4-dihydro-quinalolin-2-yl)-2-methyl-propyl]-4-methyl-benzamide, 325 g (97% yield) as a white foam solid.

1.10 (R)-N-(3-amino-propyl)-N-[1-(3-benzyl-7-chloro-4-oxo-3,4-dihydro-quinalolin-2-yl)-2-methyl-propyl]-4-methyl-benzamide, mesylate salt A dry round bottomed flask, equipped with a magnetic stirrer, dropping funnel, cooling bath and nitrogen bubbler was charged with 10 g (1 eq.) of (R)-N-(3-amino-propyl)-N-[1-(3-benzyl-7-chloro-4-oxo-3,4-dihydro-quinazolin-2-yl)-2-methyl-propyl]-4-methyl-benzamide and 50 mL of MTBE, and stirred until the benzamide was dissolved. The solution was cooled to 10° C. and slowly charged with 1.86 g (1 eq.) of methane sulfonic acid via the dropping funnel. When the addition was complete, the solution was warmed to room temperature and quickly charged with 50 mL of hexanes. The resulting solid was isolated by filtration under Nitrogen, washed with 100 mL of hexanes, and dried under vacuum at 60° C. to constant weight affording the title salt of Formula I, (R)-N-(3-amino-propyl)-N-[1-(3-benzyl-7-chloro-4-oxo-3,4-dihydro-quinazolin-2-yl)-2-methyl-propyl]-4-methyl-benzamide, mesylate salt (10.2 g, 86% yield).

Example 2

Synthesis of (S)-[1-(3-Benzyl-7-chloro-4-oxo-3,4-dihydro-quinazolin-2-yl)-2-methylpropyl]-carbamic acid tert-butyl ester 2.1 Formula 104 where $R^2$ is i-Propyl; $R^7$ is Chloro; and $R^5$, $R^6$ and $R^8$ are H A dry 3-necked, round bottomed flask, equipped with a magnetic stirrer, nitrogen inlet and an ice-bath, was charged with 250 mL of anhydrous THF, 22.82 g (0.105 mol) of dry N-Boc-L-valine (Formula 101), and 12.2 mL (0.11 mol) of anhydrous N-methylmorpholine, (99%), and was cooled to 0° C. To the stirring solution was added 14.5 mL (0.11 mol) of isobutyl chloroformate (98%) (Formula 102), over 15 min (internal temperature 5° C.) and the mixture was stirred for additional 1.5 h at 0° C. TLC analysis (hexanes/ethyl acetate 7:3) indicated complete reaction.

To the above stirring mixture at 0° C., 17.51 g (0.1 mol) of 4-chloro-anthranilic acid (98%) (Formula 103) was added in one portion and the mixture continued to stir for 2 h at 0° C. To the stirring mixture 11.1 mL (0.1 mol) of anhydrous N-methylmorpholine, (99%), was added over 15 min at 0° C. to give the title compound of Formula 104, 2-(2-tert-butoxycarbonylamino-L-3-methyl-butyrylamino)-4-chloro-benzoic acid, which was carried forward without isolation or purification. TLC analysis (hexanes/ethyl acetate 7:3) indicated complete reaction.

2.2 Formula 105 where $R^2$ is i-Propyl; $R^7$ is Chloro; and $R^5$, $R^6$ and $R^8$ are H To the stirring mixture obtained in Example 2.1 was added 13.2 mL (0.1 mol) of isobutyl chloroformate, (98%), over 15 min (internal temperature 5° C.) followed by the addition of 11 mL (0.1 mol) of anhydrous N-methylmorpholine, (99%), over 15 min at 0° C. The mixture was stirred for an additional hour at 0° C. to give the title compound of Formula 105, (S)-[1-(7-chloro-4-oxo-4H-benzo[d][1,3]oxazin-2-yl-2-methyl-propyl]-carbamic acid tert-butyl ester, which was carried forward without isolation or purification. TLC analysis (hexanes/ethyl acetate 7:3) indicated complete reaction. $^1$HNMR (300 MHz, DMSO-$d_6$) δ (ppm) 8.10(d, 1H), 7.70(m,2H), 7.45(d,1H), 4.20(t,1H), 3.85(d,1H), 2.10 (m,1H), 1.85(m,1H), 1.40–1.15(m, 9H), 1.0–0.8(m,6H).

2.3 Formula 106 where $R^1$ is Benzyl; $R^2$ is i-Propyl; $R^7$ is Chloro; and $R^5$, $R^6$ and $R^8$ are H and Formula 107 where $R^1$ is Benzyl; $R^2$ is i-Propyl; $R^{4'}$ is Boc; $R^8$ is Chloro; and $R^5$, $R^6$ and $R^9$ are H To the stirring mixture obtained in Example 2.2 was added 11.0 mL (0.1 mol) of benzylamine, (99%), over 10 minutes at 0° C. The mixture was stirred for 2 h at 0° C. at which time TLC analysis (hexanes/ethyl acetate 7:3) indicated that the reaction was less than half way complete. The mixture was then allowed to warm to room temperature and stirring continued for another 2 h. TLC analysis indicated unchanged reaction. The reaction mixture was cooled to 0° C. and additional 11.0 mL (0.1 mol) of benzylamine, (99%), was added in one portion. The mixture was allowed to stir at room temperature for an additional 2 h. TLC analysis again indicated that the reaction was approximately 80% done. Then additional 11.0 mL (0.1 mol) of benzylamine, (99%), was added in one portion at room temperature. The mixture was allowed to stir at room temperature for an additional 2 h. TLC analysis again indicated that the reaction had proceeded almost to completion, giving a mixture of Formulae 106 and 107.

The reaction mixture was then diluted with 250 mL methyl-t-butyl ether (MTBE), transferred into a separatory funnel and washed successively with 3×200 mL of water, with 2×200 mL of 1N hydrochloric acid, with 100 mL of saturated sodium bicarbonate, and with 200 mL of brine. The organic layer was passed through a 25 g cake of sodium sulfate into a round-bottomed flask. The solvent was removed by rotary evaporation and the residue was dissolved in 50 mL of MTBE. The mixture was slowly added to a Erlenmeyer flask containing 250 mL of hexanes while stirred at room temperature. Initially it became cloudy and then solid started forming. The mixture was stirred at 0° C. for 4 h. A white solid was collected and dried to afford 23.9 g (52% yield) of the title compound of Formula 106, (S)-{1-[(2-benzylcarbamoyl-5-chloro-phenylimino)-methyl]-2-methyl-propyl}-carbamic acid tert-butyl ester. $^1$HNMR (300 MHz, DMSO-$d_6$) δ (ppm) 11.90(s,1H), 9.39 (S,1H), 8.60(S,1H), 7.80(S,1H), 7.30(m,8H), 4.50(m,2H), 3.80(m,1H), 2.15(m,1H), 1.40–1.20(m,9H), 0.85(m,6H). The filtrate was concentrated to dryness and applied to a 100 g silica-gel plug pre-packed with hexanes/ethyl acetate (5:1) and eluted with 10 fractions×100 mL of hexanes/ethyl acetate (5:1). 9.2 Grams (21% yield) of the title compound of Formula 107, (S)-[1-(3-benzyl-7-chloro-4-oxo-3,4-dihydroquinazolin-2-yl)-2-methylpropyl]-carbamic acid tert-butyl ester was isolated as a white solid along with 5.1 g (11% yield) of Formula 106 as a white solid.

2.4A Formula 107 where $R^1$ is Benzyl; $R^2$ is i-Propyl; $R^{4'}$ is Boc; $R^7$ is Chloro; and $R^5$, $R^6$ and $R^8$ are H A dry 3-necked, round bottomed flask, equipped with a magnetic stirrer, nitrogen inlet, heating mantle and a water condenser, was charged with 60 mL of 1,4-dioxane/ethylene glycol (2:1), 4.60 g (10 mmol) of (S)-{1-[(2-benzylcarbamoyl-5-chloro-phenylimino)-methyl]-2-methyl-propyl}-carbamic acid tert-butyl ester (a compound of Formula 106, obtained as described in Example 2.3), and 0.46 g (11 mmol) of lithium hydroxide monohydrate. The mixture was heated to reflux and the reaction was monitored by TLC (hexanes/ethyl acetate 7:3). After 4 h of refluxing the reaction appeared to be complete. The mixture was allowed to cool to room temperature and slowly was acidified to pH=5 by adding 1N hydrochloric acid. The mixture was stirred for 1 h and the white suspension was separated by filtration and dried in high vacuum to afford 3.5 g (83% yield) of the title compound of Formula 107, (S)-[1-(3-benzyl-7-chloro-4-oxo-3,4-dihydro-quinazolin-2-yl)-2-methylpropyl]-carbamic acid tert-butyl ester [mostly the (S) enantiomer]. $^1$HNMR (300 MHz, DMSO-d$_6$) δ (ppm)8.15(d,1H), 7.65(S, 1H), 7.60(d,1H), 7.40–7.20(m,5H), 5.75(d,1H), 5.15(d,1H), 4.40(t,1H), 2.25(m,1H), 1.40–1.15(m,10H), 0.08(d,3H), 0.35(d,3H).

2.4B Formula 107 where R$^1$ is Benzyl; R$^2$ is i-Propyl; R$^{4*}$ is Boc; R$^7$ is Chloro; and R$^5$, R$^6$ and R$^8$ are H A dry 3-necked, round bottomed flask, equipped with a magnetic stirrer, gas bubbler, heating mantle and a water condenser, was charged with 545.73 g (1.19 mol) of (R)-{1-[(2-benzylcarbamoyl-5-chloro-phenylimino)-methyl]-2-methyl-propyl}-carbamic acid tert-butyl ester (a compound of Formula 106, obtained, for example, as described in Example 2.3), 520 mL of dimethoxymethane and 520 mL (2.492 mol) of HMDS. The mixture was heated to reflux for 24 hours and then allowed to cool. The volatiles were removed by rotary evaporation, leaving an oily residue that was then triturated with ethanol (3×125 mL) to remove residual HMDS or ammonia. To the resulting oil was added 400 mL of ethanol, and the mixture was heated until a homogeneous solution had been obtained. At reflux temperature, 60 mL of water was added and the solution was allowed to cool slowly with light stirring, overnight. The resulting white suspension was allowed to settle; an aliquot of the supernatant was removed and treated dropwise with water to confirm completion (no more solid was formed). The solid was filtered, washed (3×200 mL H$_2$O/EtOH (1:4)), and dried in an oven at 50° C. for 48 hours to afford 260.23 g (51% yield) of the enantiomerically pure title compound of Formula 107, (R)-[1-(3-benzyl-7-chloro-4-oxo-3,4-dihydro-quinazolin-2-yl)-2-methylpropyl]-carbamic acid tert-butyl ester.

Example 3

Synthesis of [1-(3-Benzyl-7-chloro-4-oxo-3,4-dihydro-quinazolin-2-yl)-2-methylpropyl]-carbamic acid tert-butyl ester 3.1 Formula 201 where R$^1$ is H; R$^2$ is i-Propyl; R$^7$ is Chloro; and R$^5$, R$^6$ and R$^8$ are H (S)-[1-(7-Chloro-4-oxo-4H-benzo[d][1,3]oxazin-2-yl-2-methyl-propyl]carbamic acid tert-butyl ester (a compound of Formula 105) was prepared (e.g., as described in Example 2.2) in a 3-necked, round bottom flask equipped with a magnetic stirrer, nitrogen inlet and an ice bath. A dry-ice condenser was fitted to the reaction flask and to the stirring mixture (at 0° C.) gaseous ammonia was slowly introduced until the resulting exotherm was no longer observed. The mixture was then allowed to stir for 2 h at room temperature and TLC analysis (hexanes/ethyl acetate 7:3) indicated complete reaction. The compound of Formula 105 was consumed and the title compound of Formula 201 was formed. The reaction mixture was then diluted with 250 mL of water, and was transferred into a round bottom 1-necked flask. The organic solvent was removed by rotary evaporation. The aqueous residue was carefully acidified to pH=5 with 1N hydrochloric acid. A white solid was collected and dried to afford 35 g (76% yield) of the title compound of Formula 201, (S)-{1-[(2-carbamoyl-5-chloro-phenylimino)-methyl]-2-methyl-propyl}-carbamic acid tert-butyl ester. $^1$HNMR (300 MHz, DMSO-d$_6$) δ (ppm)12.15(S,1H), 8.65 (S,1H), 8.30(S,1 H), 7.85(d,1H), 7.70(S,1H), 7.35(d,1H), 7.20(d,1H), 3.75(m,1H), 2.10(m,1H), 1.40–1.20(m.9H), 0.90(m,6H).

3.2 Formula 202 where R$^1$ is H; R$^2$ is i-Propyl; R$^7$ is Chloro; and R$^5$, R$^6$ and R$^8$ are H A dry 3-necked, round bottomed flask, equipped with a magnetic stirrer, nitrogen inlet, heating mantle, and a water condenser, was charged with 60 mL of THF, 3.70 g (10 mmol) of (S)-{1-[(2-carbamoyl-5-chloro-phenylimino)-methyl]-2-methyl-propyl}-carbamic add tert-butyl ester (the compound of Formula 201 prepared, e.g., as described in Example 3.1), and 0.46 g (11 mmol) of lithium hydroxide monohydrate. The mixture was heated to reflux and the reaction was monitored by TLC (hexanes/ethyl acetate 7:3) by which, after 1 h of refluxing, the reaction was shown to be complete. The mixture was allowed to cool to room temperature and transferred to a round bottom 1-necked flask followed by dilution with 60 mL of water. The stirring mixture was then slowly was acidified to pH=5 by adding 1N hydrochloric acid and the THF was removed by rotary evaporation. The white suspension was separated by filtration and dried in high vacuum to afford 3.5 g (100% yield) of the title compound of Formula 202, (S)-[1-(7-chloro-4-oxo-3,4-dihydro-qunazolin-2-yl)-2-methylpropyl]-carbamic acid tert-butyl ester. $^1$HNMR (300 MHz, DMSO-d$_6$) δ (ppm)8.15(d,1H), 7.65(S,1H), 7.50(d,1H), 7.00(d,1H), 4.20 (m,1H), 2.05(m,1H), 1.40–1.15(m,9H), 0.95–0.75(m,7H).

3.3 Formula 203 where R$^1$ is Benzyl; R$^2$ is i-Propyl; R$^7$ is Chloro; and R$^5$, R$^6$ and R$^8$ are H A dry 3-necked, round bottomed flask, equipped with a magnetic stirrer and nitrogen inlet, was charged with 50 mL of DMF, 3.50 g (10 mmol) of (S)-[1-(7-chloro-4-oxo-3,4-dihydro-quinazolin-2-yl)-2-methylpropyl]-carbamic acid tert-butyl ester (the compound of Formula 202 prepared, e.g., as described in Example 3.2), 1.34 mL of benzyl bromide (98%), and 3.04 g of potassium carbonate. The mixture was stirred at room temperature overnight. TLC (hexanes/ethyl acetate 7:3) indicated complete reaction. The mixture was transferred into a Erlenmeyer flask and mixed with 100 mL of water. To the stirring mixture was then added hexanes, 50 mL. The formed white solid was collected by filtration to afford the title compound of Formula 203 (S)-[1-(3-benzyl-7-chloro-4-oxo-3,4-dihydro-quinazolin-2-yl)-2-methylpropyl]-carbamic acid tert-butyl ester (also corresponding to Formula 107). The layers were separated and the organic was concentrated to dryness. The residue was chromatographed to afford an additional yield of the title compound. $^1$HNMR (300 MHz, DMSO-d$_6$) δ (ppm)8.15(d, 1H), 7.65(S,1H), 7.60(d,1H), 7.40–7.20(m,5H), 5.75(d,1H), 5.15(d,1H), 4.40(t,1H), 2.25(m,1H), 1.40–1.15(m,10H), 0.08(d, 3H), 0.35(d,3H).

Example 4

Synthesis of N-(3-Amino-propyl)-N-[1-(3-benzyl-7-chloro-4-oxo-3,4-dihydro-quinalolin-2-yl)-2-methyl-propyl]-4-methyl-benzamide 4.1 Formula 301 where R$^1$ is Benzyl; R$^2$ is i-Propyl; R$^{4*}$ is H; R$^7$ is Chloro; and R$^5$, R$^6$ and R$^8$ are H A dry 3-necked, round bottomed flask, equipped with a magnetic stirrer, nitrogen inlet, heating mantle and water condenser, was charged with 60 mL of toluene, 4.42 g (10 mmol) of (S)-[1-(3-benzyl-7-chloro-4-oxo-3,4-dihydroquinazolin-2-yl)-2-methylpropyl]-carbamic acid tert-butyl ester (the compound of Formula 107 or 203 prepared, e.g., as described in Example 2.4 or 3.3), and 4.20 g of PTSA. The mixture was heated to reflux for 1 h, during which the evolution of gas was observed. Upon cessation of gas evolution, TLC analysis (hexanes/ethyl acetate 7:3) indicated complete reaction. The mixture was cooled to room temperature, initially formed an oil that separated at the bottom of the flask and quickly solidified into a brown solid. Toluene was decanted and 50 mL of saturated potassium bicarbonate (room temperature) was added to the solid with stirring followed by the addition of 25 mL of water. The resulting white solid was collected by filtration to afford 3.3 g (96% yield) of the title compound of Formula 301, (S)-2-(1-amino-2-methyl-propyl)-3-benzyl-7-chloro-3H-quinazolin-4-one.

4.2 Formula I where $R^1$ is Benzyl; $R^2$ is i-Propyl; $R^3$ is p-Methyl-phenyl; $R^4$ is n-Propylamine; $R^7$ is Chloro; and $R^5$, $R^6$ and $R^8$ are H The (S)-2-(1-amino-2-methyl-propyl)-3-benzyl-7-chloro-3H-quinazolin-4-one obtained in Example 4.1 is carried forward as described in Examples 1.7 through 1.9 to yield the S-isomer of the title compound.

Example 5

Synthesis of (R)-[1-(3-Benzyl-7-chloro-4-oxo-3,4-dihydro-quinazolin-2-yl)-2-methylpropyl]-carbamic acid tert-butyl ester 5.1 Formula 104 where $R^2$ is i-Propyl; $R^7$ is Chloro; and $R^5$, $R^6$ and $R^8$ are H A dry 3-necked, round bottomed flask, equipped with a magnetic stirrer, nitrogen inlet and an ice-bath, is charged with 250 mL of anhydrous THF, 22.82 g (0.105 mol) of dry N-Boc-D-valine (Formula 101), and 12.2 mL (0.11 mol) of anhydrous N-methylmorpholine, (99%), and cooled to 0° C. To the stirring solution is added 14.5 mL (0.11 mol) of isobutyl chloroformate (98%) (Formula 102), over 15 min (internal temperature 5° C.) and the mixture is stirred for additional 1.5 h at 0° C. TLC analysis (hexanes/ethyl acetate 7:3) indicates complete reaction.

To the above stirring mixture at 0° C., 17.51 g (0.1 mol) of 4-chloro-anthranilic acid (98%) (Formula 103) is added in one portion and the mixture continued to stir for 2 h at 0° C. To the stirring mixture 11.1 mL (0.1 mol) of anhydrous N-methylmorpholine, (99%), is added over 15 min at 0° C. to give the title compound of Formula 104, 2-(2-tert-butoxycarbonylamino-D-3-methyl-butyrylamino)-4-chloro-benzoic acid, which is carried forward without isolation or purification. TLC analysis (hexanes/ethyl acetate 7:3) indicates complete reaction.

5.2 Formula 105 where $R^2$ is i-Propyl; $R^7$ is Chloro; and $R^5$, $R^6$ and $R^8$ are H To the stirring mixture obtained in Example 5.1 is added 13.2 mL (0.1 mol) of isobutyl chloroformate, (98%), over 15 min (internal temperature 5° C.) followed by the addition of 11.1 mL (0.1 mol) of anhydrous N-methylmorpholine, (99%), over 15 min at 0° C. The mixture is stirred for an additional hour at 0° C. to give the title compound of Formula 105, (R)-[1-(7-chloro-4-oxo-4H-benzo[d][1,3]oxazin-2-yl-2-methyl-propyl]-carbamic acid tert-butyl ester, which is carried forward without isolation or purification. TLC analysis (hexanes/ethyl acetate 7:3) indicates complete reaction.

5.3 Formula 106 where $R^1$ is Benzyl; $R^2$ is i-Propyl; $R^7$ is Chloro; and $R^5$, $R^6$ and $R^8$ are H and Formula 107 where $R^1$ is Benzyl; $R^2$ is i-Propyl; $R^{4'}$ is Boc; $R^7$ is Chloro; and $R^5$, $R^6$ and $R^8$ are H To the stirring mixture obtained in Example 5.2 is added 11.0 mL (0.1 mol) of benzylamine, (99%), over 10 minutes at 0° C. The mixture is stirred for 2 h at 0° C., then allowed to warm to room temperature and stirring continues for another 2 h, then cooled to 0° C. and additional 11.0 mL (0.1 mol) of benzylamine, (99%), is added in one portion. The mixture is allowed to stir at room temperature for an additional 2 h, then an additional 11.0 mL (0.1 mol) of benzylamine, (99%), is added in one portion at room temperature. The mixture is allowed to stir at room temperature for an additional 2 h. TLC analysis indicates that the reaction will have proceeded almost to completion, giving a mixture of Formulae 106 and 107.

The reaction mixture is then diluted with 250 mL methyl-t-butyl ether (MTBE), transferred into a separatory funnel and washed successively with 3×200 mL of water, with 2×200 mL of 1N hydrochloric acid, with 100 mL of saturated sodium bicarbonate, and with 200 mL of brine. The organic layer is passed through a 25 g cake of sodium sulfate into a round-bottomed flask. The solvent is removed by rotary evaporation and the residue dissolved in 50 mL of MTBE. The mixture is slowly added to an Erlenmeyer flask containing 250 mL of hexanes while stirred at room temperature. Initially it becomes cloudy and then solid starts forming. The mixture is stirred at 0° C. for 4 h. A white solid is collected and dried to afford the title compound of Formula 106, (R)-{1-[(2-benzylcarbamoyl-5-chloro-phenylimino)-methyl]-2-methyl-propyl}-carbamic acid tert-butyl ester. The filtrate is concentrated to dryness and applied to a 100 g silica-gel plug pre-packed with hexanes/ethyl acetate (5:1) and eluted with 10 fractions×100 mL of hexanes/ethyl acetate (5:1). The title compound of Formula 107, (R)-[1-(3-benzyl-7-chloro-4-oxo-3,4-dihydro-quinazolin-2-yl)-2-methylpropyl]-carbamic acid tert-butyl ester is isolated as a white solid along with Formula 106 as a white solid.

5.4 Formula 107 where $R^1$ is Benzyl; $R^2$ is i-Propyl; $R^{4'}$ is Boc; $R^7$ is Chloro; and $R^5$, $R^6$ and $R^8$ are H A dry 3-necked, round bottomed flask, equipped with a magnetic stirrer, nitrogen inlet, heating mantle and a water condenser, is charged with 60 mL of 1,4-dioxane/ethylene glycol (2:1), 4.60 g (10 mmol) of (R)-{1-[(2-benzylcarbamoyl-5-chloro-phenylimino)-methyl]-2-methyl-propyl}-carbamic acid tert-butyl ester (a compound of Formula 106, obtained as described in Example 5.3), and 0.46 g (11 mmol) of lithium hydroxide monohydrate. The mixture is heated to reflux and the reaction is monitored by TLC (hexanes/ethyl acetate 7:3). After 4 h of refluxing the reaction appears to be complete. The mixture is allowed to cool to room temperature and is slowly acidified to pH=5 by adding 1N hydrochloric acid. The mixture is stirred for 1 h and the white suspension is separated by filtration and dried in high vacuum to afford the title compound of Formula 107, (R)-[1-(3-benzyl-7-chloro-4-oxo-3,4-dihydro-quinazolin-2-yl)-2-methylpropyl]-carbamic acid tert-butyl ester.

Example 6

Synthesis of (R)-[1-(3-Benzyl-7-chloro-4-oxo-3,4-dihydro-quinazolin-2-yl)-2-methylpropyl]-carbamic acid tert-butyl ester 6.1 Formula 201 where $R^1$ is H; $R^2$ is i-Propyl; $R^7$ is Chloro; and $R^5$, $R^6$ and $R^8$ are H (R)-[1-(7-Chloro-4-oxo-4H-benzo[d][1,3]oxazin-2-yl-2-methyl-propyl]-carbamic acid tert-butyl ester (a compound of Formula 105) is prepared (e.g., as described in Example 5.2) in a 3-necked, round bottom flask equipped with a magnetic stirrer, nitrogen inlet and an ice bath. A dry-ice condenser is fitted to the reaction flask and to the stirring mixture (at 0° C.) gaseous ammonia is slowly introduced until the resulting exotherm is no longer observed. The mixture is then allowed to stir for 2 h at room temperature and TLC analysis (hexanes/ethyl acetate 7:3) indicates complete reaction. The compound of Formula 105 is consumed and the title compound of Formula 201 is formed. The reaction mixture is then diluted with 250 mL of water, and transferred into around bottom 1-necked flask. The organic solvent is removed by rotary evaporation. The aqueous residue is carefully acidified to pH=5 with 1N hydrochloric acid. A white solid is collected and dried to afford the title compound of Formula 201, (R)-{1-[(2-carbamoyl-5-chloro-phenylimino)-methyl]-2-methyl-propyl}-carbamic acid tert-butyl ester.

6.2 Formula 202 where $R^1$ is H; $R^2$ is i-Propyl; $R^7$ is Chloro; and $R^5$, $R^6$ and $R^8$ are H A dry 3-necked, round bottomed flask, equipped with a magnetic stirrer, nitrogen inlet, heating mantle, and a water condenser, is charged with 60 mL of THF, 3.70 g (10 mmol) of (R)-{1[(2-carbamoyl-5-chloro-phenylimino)-methyl]-2-methyl-propyl}-carbamic acid tert-butyl ester (the compound of Formula 201 prepared, e.g., as described in Example 6.1), and 0.46 g (11 mmol) of lithium hydroxide monohydrate. The mixture is heated to reflux and the reaction monitored by TLC (hexanes/ethyl acetate 7:3) by which, after 1 h of refluxing, the reaction is shown to be complete. The mixture is allowed to cool to room temperature and transferred to a round bottom 1-necked flask followed by dilution with 60 mL of water. The stirring mixture is then slowly acidified to pH=5 by adding 1N hydrochloric acid and the THF is removed by rotary evaporation. The white suspension is separated by filtration and dried in high vacuum to afford the title compound of Formula 202, (R)-[1-(7-chloro-4-oxo-3,4-dihydro-quinazolin-2-yl)-2-methylpropyl]-carbamic acid tert-butyl ester.

6.3 Formula 203 where $R^1$ is Benzyl; $R^2$ is i-Propyl; $R^7$ is Chloro; and $R^5$, $R^6$ and $R^8$ are H A dry 3-necked, round bottomed flask, equipped with a magnetic stirrer and nitrogen inlet, is charged with 50 mL of DMF, 3.50 g (10 mmol) of (R)-[1-(7-chloro-4-oxo-3,4-dihydro-quinazolin-2-yl)-2-methylpropyl]-carbamic acid tert-butyl ester (the compound of Formula 202 prepared, e.g., as described in Example 6.2), 1.34 mL of benzyl bromide (98%), and 3.04 g of potassium carbonate. The mixture is stirred at room temperature overnight. TLC (hexanes/ethyl acetate 7:3) indicates complete reaction. The mixture is transferred into a Erlenmeyer flask and mixed with 100 mL of water. To the stirring mixture is then added hexanes, 50 mL. The formed white solid is collected by filtration to afford the title compound of Formula 203 (R)-[1-(3-benzyl-7-chloro-4-oxo-3,4-dihydro-quinazolin-2-yl)-2-methylpropyl]-carbamic acid tert-butyl ester (also corresponding to Formula 107). The layers are separated and the organic is concentrated to dryness. The residue is chromatographed to afford an additional yield of the title compound.

Example 7

Synthesis of (R)-N-(3-Amino-propyl)-N-[1-(3-benzyl-7-chloro-4-oxo-3,4-dihydro-quinalolin-2-yl)-2-methyl-propyl]-4-methyl-benzamide 7.1 Formula 301 where $R^1$ is Benzyl; $R^2$ is i-Propyl; $R^{4'}$ is H; $R^7$ is Chloro; and $R^5$, $R^6$ and $R^8$ are H A dry 3-necked, round bottomed flask, equipped with a magnetic stirrer, nitrogen inlet, heating mantle and water condenser, is charged with 60 mL of toluene, 4.42 g (10 mmol) of (R)-[1-(3-benzyl-7-chloro-4-oxo-3,4-dihydro-quinazolin-2-yl)-2-methylpropyl]-carbamic acid tert-butyl ester (the compound of Formula 107 or 203 prepared, e.g., as described in Example 6.4 or 6.3), and 4.20 g of PTSA. The mixture is heated to reflux for 1 h, during which the evolution of gas is observed. Upon cessation of gas evolution, TLC analysis (hexanes/ethyl acetate 7:3) indicates complete reaction. The mixture is cooled to room temperature, initially forms an oil that separates at the bottom of the flask and quickly solidifies into a brown solid. Toluene is decanted and 50 mL of saturated potassium bicarbonate (room temperature) is added to the solid with stirring followed by the addition of 25 mL of water. The resulting white solid is collected by filtration to afford the title compound of Formula 301, (R)-2-(1-amino-2-methyl-propyl)-3-benzyl-7-chloro-3H-quinazolin-4-one.

7.2 Formula I where $R^1$ is Benzyl; $R^2$ is i-Propyl; $R^3$ is p-Methyl-phenyl; $R^4$ is n-Propylamine; $R^7$ is Chloro; and $R^5$, $R^6$ and $R^8$ are H The (R)-2-(1-amino-2-methyl-propyl)-3-benzyl-7-chloro-3H-quinazolin-4-one obtained in Example 7.1 is carried forward as described in Examples 1.7 through 1.9 to yield the (R)-isomer of the title compound.

Example 8

8.1 Formula 402 where $R^2$ is i-Propyl; and $R^{4'}$ is n-Propyl-NHBoc

A solution of 2-bromo-3-methyl-butyric acid ethyl ester in EtOH (0.3 M) is treated with 1.1 eq of n-propyl-HNBoc-amine and the mixture stirred overnight. The solvents are evaporated and the residue re-dissolved in dichloromethane and washed with 3% NaOH. The organics are dried over sodium sulfate, filtered and evaporated to dryness to give the corresponding crude title compound of Formula 402.

8.2 Formula 403 where $R^2$ is i-Propyl; $R^3$ is p-Methyl-phenyl; and $R^{4'}$ is n-Propyl-NHBoc The crude compound of Formula 402, prepared, e.g., as in Example 8.1, is dissolved in dichloromethane to a concentration of 0.25 M and treated with 1.1 eq of p-toluoyl chloride and 1.1 eq of triethylamine. The mixture is stirred overnight and washed with 3% NaOH. The mixture is dried over sodium sulfate, filtered and evaporated. The title compound of Formula 403 is purified over silica gel using EtOAc/hexanes as eluent.

8.3 Formula 404 where $R^2$ is i-Propyl; $R^3$ is p-Methyl-phenyl; $R^{4'}$ is n-Propyl-NHBoc; $R^7$ is Chloro; and $R^5$, $R^6$ and $R^8$ are H The compound of Formula 403, prepared, e.g., as in Example 8.2, is dissolved in THF to a concentration of 0.5 M and then treated with 6 eq of LiOH dissolved in water to a concentration of 1 M. The mixture is stirred overnight and then evaporated to dryness. The residue is triturated with dichloromethane, dried over sodium sulfate, filtered and evaporated to give crude lithium salt. The lithium salt is dissolved in DMF to a concentration of 0.3 M and treated with 1.5 eq of PyBroP and 1.1 eq of 2-amino-4-chloro benzoic acid methyl ester. The mixture is stirred overnight and washed with 3% NaOH. The mixture is dried over sodium sulfate, filtered and evaporated. The crude title compound of Formula 404 is purified over silica gel using EtOAc/hexanes as eluent.

8.4 Formula 405 where $R^2$ is i-Propyl; $R^3$ is p-Methyl-phenyl; $R^{4'}$ is n-Propyl-NHBoc; $R^7$ is Chloro; and $R^5$, $R^6$ and $R^8$ are H The compound of Formula 404, prepared, e.g., as in Example 8.3, is dissolved in THF to a concentration of 0.5 M and then treated with 6 eq of LiOH dissolved in water to a concentration of 1 M. The mixture is stirred overnight and then evaporated to dryness. The residue is triturated with dichloromethane, dried over sodium sulfate, filtered and evaporated to give the crude title compound of Formula 405 as a lithium salt.

8.5 Formula 406 where $R^2$ is i-Propyl; $R^3$ is p-Methyl-phenyl; $R^{4'}$ is n-Propyl-NHBoc; $R^7$ is Chloro; and $R^5$, $R^6$ and $R^8$ are H The lithium salt of Formula 405, prepared, e.g., as in Example 8.4, is dissolved in DMF to a concentration of 0.3 M and treated with 1.4 eq of PyBroP, 0.2 eq of triethylamine and 1.2 eq of benzylamine. The mixture is stirred overnight and washed with 3% NaOH. The mixture is dried over sodium sulfate, filtered and evaporated. The crude title compound of Formula 406 is purified over silica gel using EtOAc/hexanes as eluent.

8.6 Formula 407 where $R^1$ is Benzyl; $R^2$ is i-Propyl; $R^3$ is p-Methyl-phenyl; $R^{4'}$ is n-Propyl-NHB $R^7$ is Chloro; and $R^5$, $R^6$ and $R^8$ are H The compound of Formula 406, prepared, e.g., as in Example 8.5, is mixed with ethylene glycol to a concentration of 0.1 M and to this is added 2 eq of KOH. The mixture is stirred at 110 C overnight. After cooling to room temperature, the mixture is diluted with EtOAc and washed with NaHCO3. The solvent is dried over sodium sulfate, filtered and evaporated to dryness. The residue is purified over silica gel with EtOAc/hexanes as eluent.

8.7 Formula I where $R^1$ is Benzyl; $R^2$ is i-Propyl; $R^3$ is p-Methyl-phenyl; $R^4$ is n-Propylamine; $R^7$ is Chloro; and $R^5$, $R^6$ and $R^8$ are H The compound of Formula 407, prepared, e.g., as in Example 8.6, is dissolved in a 95/5 mixture of TFA/water to a concentration of 0.2 M. After stirring 30 min, the mixture is evaporated to dryness. The residue is partitioned between EtOAc and NaHCO₃ solution, dried over sodium sulfate, filtered and evaporated to give pure title compound of Formula I.

While the present invention has been described with reference to the specific embodiments thereof, it should be understood by those skilled in the art that various changes can be made and equivalents can be substituted without departing from the true spirit and scope of the invention. In addition, many modifications can be made to adapt a particular situation, material, composition of matter, process, process step or steps, to the objective, spirit and scope of the present invention. All such modifications are intended to be within the scope of the claims appended hereto. All patents and publications cited above are hereby incorporated by reference.

What is claimed is:

1. A composition of matter comprising an enantiomerically pure compound represented by Formula I:

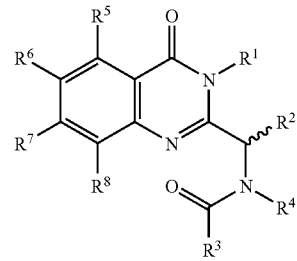

Formula I where:
$R^1$ is hydrogen, alkyl, aryl, alkylaryl, heteroaryl, alkylheteroaryl, substituted alkyl, substituted aryl, substituted alkylaryl, substituted heteroaryl or substituted alkylheteroaryl;

$R^2$ is alkyl, oxaalkyl, aryl, alkylaryl, heteroaryl, alkylheteroaryl, substituted alkyl, substituted aryl, substituted alkylaryl, substituted heteroaryl or substituted alkylheteroaryl;

$R^3$ is hydrogen, alkyl, aryl, alkylaryl, heteroaryl, alkylheteroaryl, substituted alkyl, substituted aryl, substituted alkylaryl, substituted heteroaryl, substituted alkylheteroaryl, oxaalkyl, oxaalkylaryl, substituted oxaalkylaryl, $R^9O$— or $R^9$—NH—;

$R^4$ is hydrogen, alkyl, aryl, alkylaryl, heteroaryl, alkylheteroaryl, substituted alkyl, substituted aryl, substituted alkylaryl, substituted heteroaryl or substituted alkylheteroaryl;

$R^5$, $R^6$, $R^7$ and $R^8$ are independently hydrogen, hydroxy, alkyl, alkoxy, halogen, fluoroalkyl, nitro, cyano, substituted alkyl, amino, alkylamino, dialkylamino, alkylsulfonyl, alkylsulfonamido, sulfonamidoalkyl, sulfonamidoaryl, alkylthio, carboxyalkyl, carboxamido, aminocarbonyl, aryl or heretoaryl; and $R^9$ is alkyl, aryl, alkylaryl, heteroaryl, alkylheteroaryl, substituted alkyl, substituted aryl, substituted alkylaryl, substituted heteroaryl or substituted alkylheteroaryl, or a pharmaceutically acceptable salt thereof, having a detectable amount of one or more of the following:

A) an enantiomerically pure compound of Formula 101:

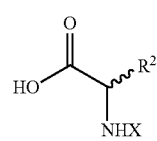

101 where X is hydrogen or a protecting group;
B) a compound of Formula 103:

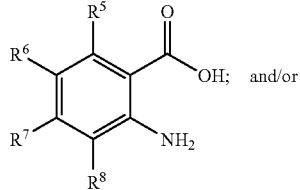

C) a cyclo-dehydration reagent chosen from HMDS, phosphorous oxychloride, oxalyl chloride, thionyl chloride, Burgess' reagent, $Ph_3P/I_2$, a Vilsmeier reagent, and lithium hydroxide monohydrate.

2. The composition of matter of claim 1 containing a detectable amount of a naturally occurring or substituted, optionally N-protected amino acid.

3. The composition of matter of claim 2 containing a detectable amount of valine.

4. The composition of matter of claim 2 containing a detectable amount of D-valine or an N-protected D-valine.

5. The composition of matter of claim 1, wherein:
$R^1$ is alkylaryl or substituted alkylaryl;
$R^2$ is lower alkyl or substituted lower alkyl;
$R^3$ is alkyl, substituted alkyl, aryl, substituted aryl, alkylaryl, alkylheteroaryl, oxaalkylaryl, oxaalkylheteroaryl, substituted alkylaryl, substituted alkylheteroaryl, substituted oxaalkylaryl or substituted oxaalkylheteroaryl;
$R^4$ is substituted alkyl;
$R^5$, $R^6$, $R^7$ and $R^8$ are hydrogen, halo, lower alkyl, substituted lower alkyl, lower alkoxy, alkylthio or cyano; and
X is Boc, CBZ, phthalide, alloc, or teoc.

6. The composition of matter of claim 5, wherein:
$R^1$ is benzyl or substituted benzyl;
for $R^2$, lower alkyl is ethyl, i-propyl, c-propyl, t-butyl or c-pentyl, and substituted lower alkyl is methylthiomethyl;
for $R^3$, is alkyl is lower alkyl; substituted alkyl is alkoxyalkyl or heterocycloalkyl; aryl is phenyl; substituted aryl is lower alkyl-, lower alkoxy- and/or halo-substituted phenyl; alkylaryl is benzyl or phenylvinyl; oxaalkylaryl is phenoxy lower alkyl; substituted alkylaryl is substituted benzyl or substituted phenylvinyl; and substituted oxaalkylaryl is substituted phenoxy lower alkyl;
$R^4$ is a primary-, secondary- or tertiary-amino-substituted lower alkyl; and
$R^5$, $R^6$, $R^7$ and $R^8$ are hydrogen, chloro, fluoro, methyl, substituted lower alkyl, methoxy, methylthio or cyano.

7. The composition of matter of claim 6, wherein:
$R^1$ is benzyl;
$R^2$ is ethyl, i-propyl, c-propyl or t-butyl;
$R^3$ is aryl is pheny or lower alkyl-, lower alkoxy- and/or halo-substituted phenyl;
$R^4$ is a primary-, secondary- or tertiary-amino-substituted lower alkyl; and
$R^5$, $R^6$, $R^7$ and $R^8$ are hydrogen, chloro, fluoro, methyl, methoxy, methylthio or cyano.

8. The composition of matter of claim 1 containing a detectable amount of HMDS.

9. The composition of matter of claim 1, which is an enantiomerically pure compound of Formula I-(R):

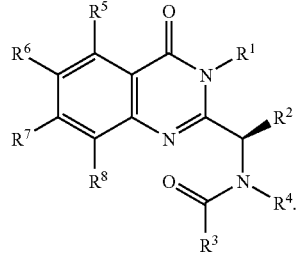

10. The composition of matter of claim 4, which is an enantiomerically pure compound of Formula I-(R):

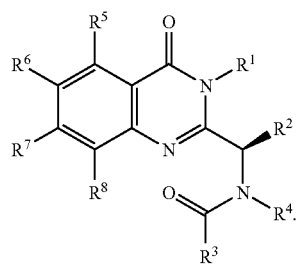

11. The composition of matter of claim 7, which is an enantiomerically pure compound of Formula I-(R):

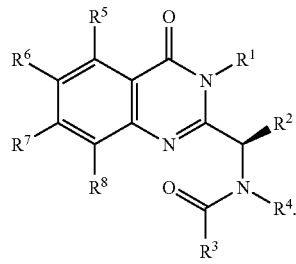

12. The composition of matter of claim 8, which is an enantiomerically pure compound of Formula I-(R):

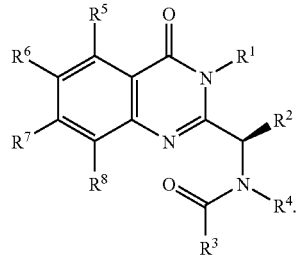

* * * * *